United States Patent
Evans et al.

(10) Patent No.: US 10,358,397 B2
(45) Date of Patent: Jul. 23, 2019

(54) PRODUCTION OF OLEFIN DIMERS

(71) Applicant: ExxonMobil Chemical Patents Inc., Baytown, TX (US)

(72) Inventors: Meagan E. Evans, Jersey City, NY (US); Crisita Carmen H. Atienza, Houston, TX (US); Jo Ann M. Canich, Houston, TX (US); John R. Hagadorn, Houston, TX (US); David A. Cano, Houston, TX (US); Gregory S. Day, College Station, TX (US); Patrick C. Chen, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/948,323

(22) Filed: Apr. 9, 2018

(65) Prior Publication Data
US 2019/0002366 A1 Jan. 3, 2019

Related U.S. Application Data

(60) Provisional application No. 62/526,766, filed on Jun. 29, 2017.

(51) Int. Cl.
| | | |
|---|---|---|
| *C07C 2/32* | (2006.01) | |
| *B01J 31/22* | (2006.01) | |
| *C10G 50/00* | (2006.01) | |

(52) U.S. Cl.
CPC ............ *C07C 2/32* (2013.01); *B01J 31/226* (2013.01); *C10G 50/00* (2013.01);
(Continued)

(58) Field of Classification Search
None
See application file for complete search history.

(56) References Cited

U.S. PATENT DOCUMENTS

| | | |
|---|---|---|
| 8,071,701 B2 | 12/2011 | Klosin et al. |
| 8,383,753 B2 | 2/2013 | Klosin et al. |

(Continued)

FOREIGN PATENT DOCUMENTS

| | | |
|---|---|---|
| JP | 2013-053309 | 3/2013 |
| JP | 2013-166735 | 8/2013 |

(Continued)

OTHER PUBLICATIONS

English translation of WO-2013022108-A1 (Year: 2013).*
(Continued)

*Primary Examiner* — In Suk C Bullock
*Assistant Examiner* — Ali Z Fadhel

(57) ABSTRACT

A process for producing alpha-olefin dimers comprises contacting, at a temperature of 80° C. or more, a feedstock comprising at least one $C_{8+}$ (linear) alpha-olefin with a catalyst system comprising activator and one or more catalyst compounds represented by the formula:

(Continued)

Table 2, Experiment 2-1 where M is a Group 4 metal; n is 1, 2, or 3; $R^4$ is hydrogen or a $C_1$ to $C_{10}$ alkyl; each of $R^1$, $R^2$, $R^3$, $R^4$, $R^5$, $R^6$, $R^7$, and $R^8$ is independently selected from hydrogen and $C_1$ to $C_{10}$ alkyl; each X is independently selected from the group consisting of hydrocarbyl radicals having from 1 to 20 carbon atoms, hydrides, amides, alkoxides, sulfides, phosphides, halides, and a combination thereof, (two X's may form a part of a fused ring or a ring system), the contacting being conducted under conditions effective to oligomerize at least part of $C_{8+}$ alpha-olefin to produce an oligomerized product containing at least 30 wt % of the alpha-olefin dimer and at least 80 mol % of vinylidene unsaturation, where the conversion of the alpha olefin is at least 10 wt %, based upon the weight of the alpha olefin monomer entering the reactor and the weight of dimer produced.

44 Claims, 3 Drawing Sheets

(52) U.S. Cl.
CPC ........ *B01J 2231/20* (2013.01); *B01J 2531/48* (2013.01); *B01J 2531/49* (2013.01); *C07C 2531/14* (2013.01); *C07C 2531/22* (2013.01)

(56) References Cited

U.S. PATENT DOCUMENTS

| | | |
|---|---|---|
| 2013/0041119 A1 | 2/2013 | Ochi et al. |
| 2013/0090273 A1 | 4/2013 | Martin et al. |
| 2014/0163173 A1 | 4/2014 | Ishiwata et al. |
| 2014/0176537 A1 | 6/2014 | Densham |
| 2014/0275429 A1 | 9/2014 | Koji et al. |
| 2014/0275664 A1 | 9/2014 | Yang et al. |

FOREIGN PATENT DOCUMENTS

| | | | |
|---|---|---|---|
| JP | 2013-166897 | 8/2013 | |
| JP | 2013-166898 | 8/2013 | |
| JP | 2014-198744 | 10/2014 | |
| WO | 2012/111777 | 8/2012 | |
| WO | 2012/111778 | 8/2012 | |
| WO | 2012/111779 | 8/2012 | |
| WO | 2012/111780 | 8/2012 | |
| WO | 2013/022108 | 2/2013 | |
| WO | WO-2013022108 A1 * | 2/2013 | ............ C08F 10/00 |

OTHER PUBLICATIONS

Nakata et al., "Completely Isospecific Polymerization of 1-Hexene Catalyzed by Hafnium(IV) Dichloro Complex Incorporating with an [OSSO]-type Bis(phenolate) Ligand," Topics in Catalysis, 2014, vol. 57, Nos. 10-13, pp. 918-922.

Nakata et al., "Controlled Isospecific Polymerization of a Alpha-Olefins by Hafnium Complex Incorporating with a Trans-Cyclooctanediyl-Birdges [OSSO]-Type Bis(phenolate) Ligand," Macromolecules, 2013, vol. 46, No. 17, pp. 6758-6764.

Ishii et al., "Zirconium Complex of an [OSSO]-Type Diphenolate Ligand Bearing trans-1,2-Cyclooctanediylbis(thio) Core: Synthesis, Structure, and Isospecific 1-Hexene Polymerization," Journal of the American Chemical Society, 2009, vol. 131, No. 38, pp. 13566-13567.

Lian et al., "Regioselective 1-Hexene Oligomerization Using Cationic Bis(phenolate) Group 4 Metal Catalysts: Switch from 1,2- to 2,1-Insertion," Angewandte Chemie, 2007, vol. 46, No. 44, pp. 8507-8510.

Capacchione et al., "Ancillary Ligand Effect on Single-Site Styrene Polymerization: Isospecificity of Group 4 Metal Bis(phenolate) Catalysts," Journal of the American Chemical Society, 2003, vol. 125, No. 17, pp. 4964-4965.

\* cited by examiner

PRODUCTION OF OLEFIN DIMERS

PRIORITY CLAIM

This application claims priority to and the benefit of U.S. Ser. No. 62/526,766, filed Jun. 29, 2017 and is incorporated by reference in its entirety.

FIELD OF THE INVENTION

This invention relates to a process for producing dimers of $C_{8+}$ alpha-olefins and to use of the resultant dimers.

BACKGROUND OF THE INVENTION $C_{8+}$ alpha-olefin dimers are attractive feedstocks for the production of waxes, lubricant additives, and basestocks. The dimeric products, which contain high levels of vinylidene unsaturation, are also desirable for use as reactive feedstocks for the production of surfactants, detergents, dispersants, and other additives.

Olefin dimerization reactions are typically carried out by contacting the desired alpha-olefin (typically decene) with a dimerization catalyst. Oligomerization of 1-decene tends to produce dimers, trimers, and tetramers, with 20, 30, and 40 carbon atoms in the molecule, respectively, such that the final reaction product has a fairly wide spectrum of molecular weight. There is, therefore, a significant need in developing catalysts which will dimerize $C_{8+}$ alpha-olefins with high yield and high selectivity.

Although generally employed in the production of high molecular weight ($>10^5$ g/mol) polymers, certain metallocene and other single site catalysts have been used to produce lower molecular weight ($<10^4$ g/mol) polymers and oligomers. For example, U.S. Pat. No. 8,071,701 discloses at Table 4, PP17, PP22, and PP27, propylene polymerization of low activity at 75° C. using trityltetrakis(pentafluorophenyl) borate and a metal complex that is the combination of Zr(benzyl)$_4$ and a ligand having the formula:

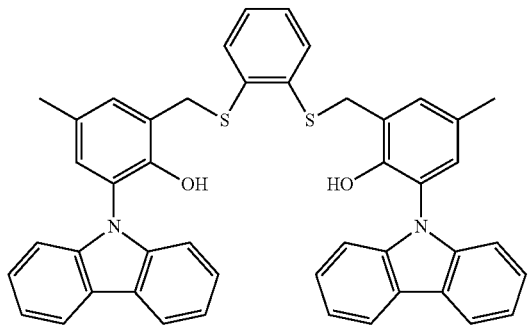

A12

Other references of interest include: US 2014/163173; US 2014/275429; WO 2012/111777; WO 2012/111778; WO 2012/111779; WO 2012/111780; WO 2013/022108; JP 2013-053309A2; JP 2013-166735A2; JP 2013-166897A; JP 2013-166898A; JP 2014-198744A; Topics in Catalysis (2014), 57(10-13), 918-922 (*Completely Isospecific Polymerization of 1-Hexene Catalyzed by Hafnium(IV) Dichloro Complex Incorporating with an [OSSO]-type Bis(phenolate) Ligand*, Nakata, Norio et al.); Macromolecules (2013), 46(17), 6758-6764 (*Controlled Isospecific Polymerization of a-Olefins by Hafnium Complex Incorporating with a trans-Cyclooctanediyl-Bridged [OSSO]-Type Bis(phenolate) Ligand*, Nakata, Norio, et al.).

According to the present invention, it has now been found that certain transition metal complexes of tetradentate [OSSO]-type bisphenolate ligands show unusual selectivity and conversion for the production of dimers of $C_{8+}$ alpha-olefins.

SUMMARY OF THE INVENTION

Thus, in one aspect, the present invention resides in a process for producing alpha-olefin dimers, the process comprising: contacting, at a temperature of 80° C. or more, one or more $C_{8+}$ alpha-olefins (preferably linear alpha-olefins) with a catalyst system comprising activator and one or more catalyst compounds represented by the formula:

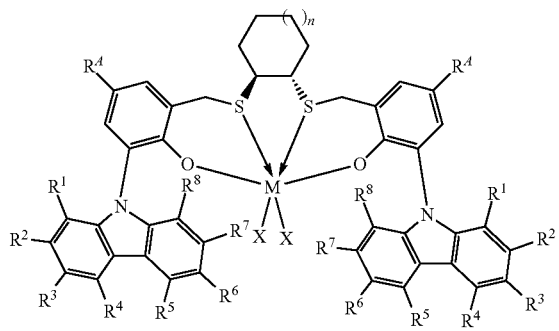

where each X is independently selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's may form a part of a fused ring or a ring system), preferably each X is independently selected from halides and $C_1$ to $C_5$ alkyl groups, benzyl, substituted benzyl, preferably each X is a methyl group or benzyl group;
M is a Group 4 metal; n is 1, 2, or 3; $R^A$ is hydrogen or a $C_1$ to $C_{10}$ alkyl; each of $R^1$, $R^2$, $R^3$, $R^4$, $R^5$, $R^6$, $R^7$, and $R^8$ is independently selected from hydrogen and $C_1$ to $C_{10}$ alkyl, optionally any two or more adjacent groups from $R^1$ to $R^8$ may be joined to form a cyclic or polycyclic ring structure; the contacting being conducted under conditions effective to oligomerize at least part of $C_{8+}$ alpha-olefin (preferably linear alpha-olefin) to produce an oligomerized product containing at least 30% by weight of the alpha-olefin dimer.

In a further aspect, the invention relates to oligomerized compositions produced by the process described herein.

DETAILED DESCRIPTION

Definitions

Figure 1:
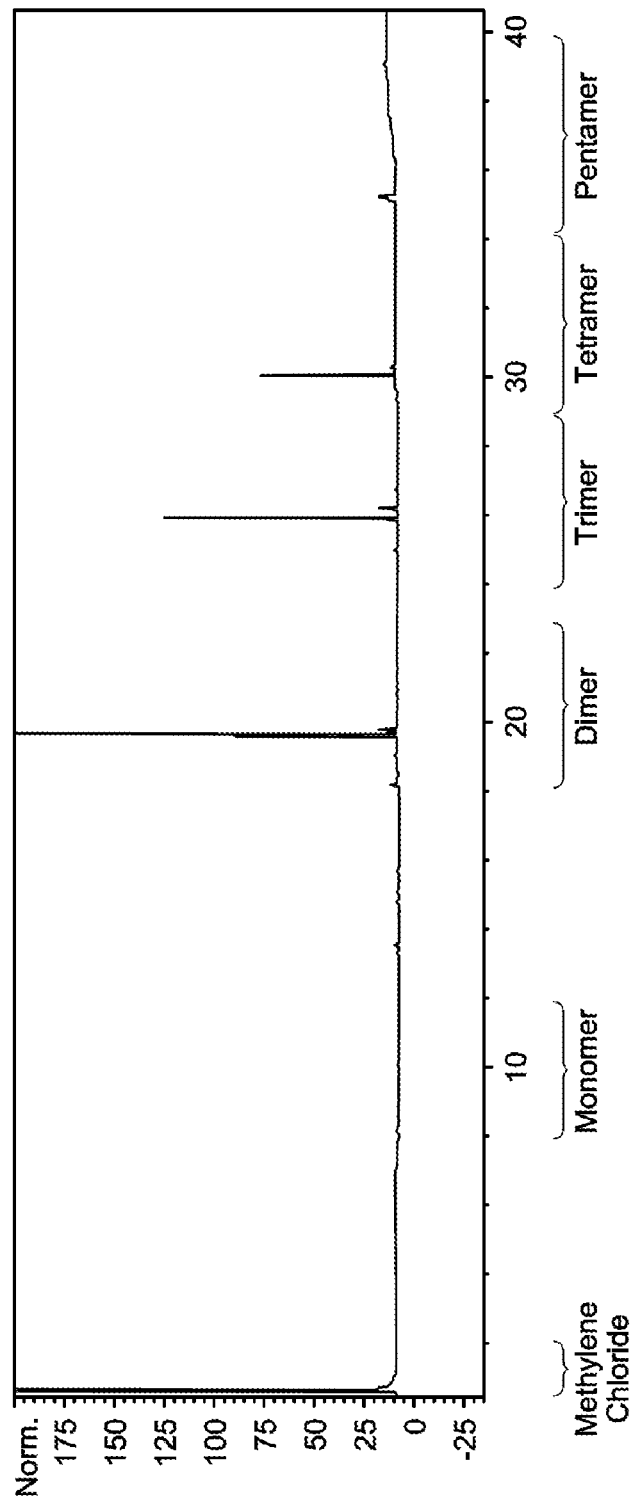
FIG. 1 is a gas chromatogram of the oligomerized product obtained in Table 2, Experiment 2-1, made from pure 1-tetradecene.

For the purposes of this invention and the claims thereto, the new numbering scheme for the Periodic Table Groups is used as described in CHEMICAL AND ENGINEERING NEWS, 63(5), pg. 27 (1985). Therefore, a "group 4 metal" is an element from group 4 of the Periodic Table, e.g., Hf, Ti, or Zr.

An "olefin," alternately referred to as "alkene," is a linear, branched, or cyclic compound of carbon and hydrogen having at least one carbon-carbon double bond. An "alpha-olefin" is an olefin having a carbon-carbon double bond which starts at the α-carbon atom, i.e., the double bond is between the #1 and #2 carbon atoms.

The term "$C_n$" olefin wherein n is a positive integer, e.g., 1, 2, 3, 4, 5, etc., as used herein means an olefin having n number of carbon atom(s) per molecule. The term "$C_{n+}$" olefin wherein n is a positive integer, e.g., 1, 2, 3, 4, 5, etc., as used herein means an olefin having at least n number of carbon atom(s) per molecule. The term "$C_{n-}$" olefin wherein n is an positive integer, e.g., 1, 2, 3, 4, 5, etc., as used herein means an olefin having no more than n number of carbon atom(s) per molecule.

As used herein, the term "aromatic" refers to hydrocarbyl groups having a planar unsaturated ring of atoms that is stabilized by an interaction of the bonds forming the ring, typically benzene, cyclopentadiene, or a derivative thereof. The term "non-aromatic" means linear, saturated cyclic or partially unsaturated cyclic group.

For purposes of this specification and the claims appended thereto, when a polymer or oligomer is referred to as comprising an olefin, the olefin present in such polymer or oligomer is the polymerized form of the olefin. A "polymer" has two or more of the same or different mer units. An oligomer is a polymer having a low molecular weight, such an Mn of less than 25,000 g/mol, or less than 10,000 g/mol, or less than 2,500 g/mol or from 200 to 25,000 g/mol, alternately from 220 to 10,000 g/mol (as determined by $^1$H NMR), or a low number of mer units, such as 75 mer units or less or 50 mer units or less, or 25 mers or less, alternately from 2 to 75 mer units, alternately from 3 to 50 mer units, alternately from 2 to 10 mer units, alternately from 2 to 5 mer units. A dimer is a polymer having two mer units of monomer, typically two mer units of the same monomer; a trimer is a polymer having three mer units of monomer, typically three mer units of the same monomer; a tetramer is a polymer having four mer units of monomer, typically four mer units of the same monomer, and so on.

The terms "alkyl radical," and "alkyl" are used interchangeably throughout this document. Likewise, the terms "group," "radical," and "substituent" are also used interchangeably in this document. For purposes of this disclosure, alkyl radical may be linear, branched, or cyclic, and when cyclic, aromatic or non-aromatic, whereas aliphatic radicals are non-aromatic alkyl radicals. Examples of each of such radicals include, but are not limited to, methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like, including their substituted analogues.

The term a "catalyst system" is used herein to refer to a combination of at least one catalyst compound, at least one activator, an optional co-activator, and an optional support material. The catalyst compound employed herein is a particular complex of a group 4 transition metal. The term complex is used to describe a molecule in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator which is believed to create a cation as a result of the removal of an anionic group, often referred to as a leaving group, from the transition metal.

A "non-coordinating anion" (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments, a co-activator can be pre-mixed with the transition metal compound to form an alkylated transition metal compound.

As used herein, Mn is number average molecular weight, Mw is weight average molecular weight, and Mz is z average molecular weight, wt % is weight percent, and mol % is mole percent. Molecular weight distribution (MWD), also referred to as polydispersity index (PDI), is defined to be Mw divided by Mn. Unless otherwise noted, all molecular weight units (e.g., Mw, Mn, Mz) are g/mol.

The following abbreviations may be used herein: Me is methyl, Et is ethyl, Pr is propyl, cPr is cyclopropyl, nPr is n-propyl, iPr is isopropyl, Bu is butyl, nBu is normal butyl, iBu is isobutyl, sBu is sec-butyl, tBu is tert-butyl, Oct is octyl, Ph is phenyl, Bn is benzyl (i.e., $CH_2Ph$), MAO is methylalumoxane, RT is room temperature (and is 23° C. unless otherwise indicated).

This invention relates to a process for producing alpha-olefin dimers, the process comprising: contacting, at a temperature of 80° C. or more (preferably from 80° C. to 200° C. preferably 85° C. to 160° C., preferably 90° C. to 150° C., preferably 100° C. to 150° C., preferably 110° C. to 150° C.), one or more $C_8$ to $C_{30}$ alpha-olefins, preferably linear alpha-olefins (alternately $C_{10}$ to $C_{24}$, alternately $C_{10}$ to $C_{20}$, alternately $C_{10}$ to $C_{14}$ alpha olefins, preferably linear alpha-olefins) with a catalyst system comprising activator (such as a non-coordinating anion activator and or an alumoxane), and one or more catalyst compounds represented by the formula:

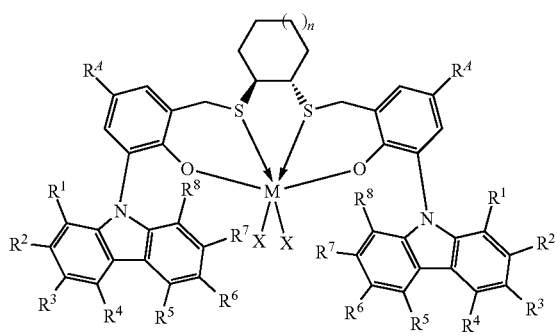

where M is a Group 4 metal; n is 1, 2, or 3; $R^A$ is hydrogen or a $C_1$ to $C_{10}$ alkyl; each of $R^1$, $R^2$, $R^3$, $R^4$, $R^5$, $R^6$, $R^7$, and $R^8$ is independently selected from hydrogen and $C_1$ to $C_{10}$ alkyl, optionally any two or more adjacent groups from $R^1$ to $R^8$ may be joined to form a cyclic or polycyclic ring structure; each X is independently selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's may form a part of a fused ring or a ring system), preferably each X is independently selected from halides and $C_1$ to $C_5$ alkyl groups, benzyl, substituted benzyl, preferably each X is a methyl group or benzyl group, the contacting being conducted under conditions effective to oligomerize at least part of the alpha-olefin (preferably linear alpha-olefin) to produce product containing at least 30% by weight of the alpha-olefin dimer, preferably linear alpha-olefin dimer, (alternately at least 40 wt %, preferably at least 50 wt %) and having at least 80 mol % (alternately at least 90 mol %, preferably 90 to 100 mol %, preferably 95 to 99 mol %) of vinylidene unsaturation, where the conversion of the alpha olefin is at least 10 wt % (alternately at least 25 wt %, alternately 25 to 100 wt %, preferably 30 to 70 wt %), based upon the weight of the alpha olefin monomer entering the reactor and the weight of the dimer produced. "Conversion" is the amount of monomer that is converted to product, and is reported as wt % and is calculated based on the product yield and the amount of monomer fed into the reactor. Unless otherwise indicated, monomer conversion and dimer selectivity are reported as weight %.

Vinyl, vinylene, trisubstituted, and vinylidene unsaturation are determined according to the $^1$H NMR method described in the Experimental section and are reported as mol %, unless otherwise indicated. Vinylidene chain ends are reported as a molar percentage of the total number of moles of unsaturated groups (that is, the sum of vinyl chain ends, vinylidene chain ends, vinylene chain ends and tri-substituteds).

In a useful embodiment, the monomers used in the oligomerization reaction are not aromatic.

In a useful embodiment, the monomers used in the oligomerization reaction are not vinyl aromatic.

Catalyst Compounds

The catalyst compounds employed in the process of the present invention comprise one or more compounds represented by the formula:

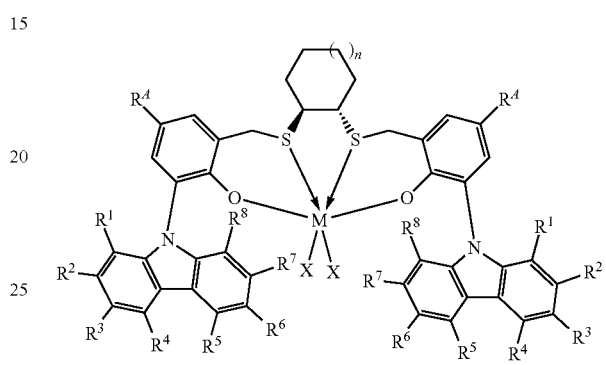

where M is a Group 4 metal, such as Zr, Ti or Hf, preferably Zr or Hf, more preferably Zr; n is 1, 2, or 3; $R^A$ is hydrogen or a $C_1$ to $C_{10}$ alkyl; each of $R^1$, $R^2$, $R^3$, $R^4$, $R^5$, $R^6$, $R^7$, and $R^8$ is independently selected from hydrogen and $C_1$ to $C_{10}$ alkyl, optionally wherein any two or more adjacent groups from $R^1$ through $R^8$ may be joined to form a cyclic or polycyclic ring structure. Suitable examples of $R^A$ and each of $R^1$, $R^2$, $R^3$, $R^4$, $R^5$, $R^6$, $R^7$, and $R^8$ are independently selected from hydrogen, methyl, ethyl, propyl, butyl, pentyl, hexyl, and isomers thereof and preferably are hydrogen and t-butyl. Most preferably, each of $R^3$ and $R^6$ is t-butyl; each X is independently selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's may form a part of a fused ring or a ring system), preferably each X is independently selected from $C_1$ to $C_5$ alkyl groups, benzyl, substituted benzyl, preferably each X is a methyl group or benzyl group. In some embodiments of the invention, each X is benzyl.

In some embodiments of the invention, n is preferably 1.

In some embodiments of the invention, n is preferably 2 or 3.

In some embodiments of the invention, $R^A$ is preferably t-butyl.

In some embodiments of the invention, $R^1$, $R^2$, $R^4$, $R^5$, $R^7$, and $R^8$ are hydrogen and $R^3$ and $R^6$ are $C_1$ to $C_{10}$ alkyl.

Catalyst compounds that are particularly useful in this invention include one or more of:
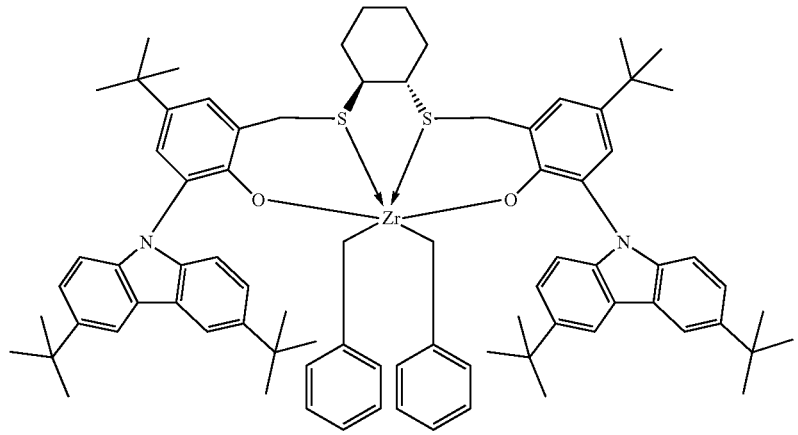
Catalyst 1
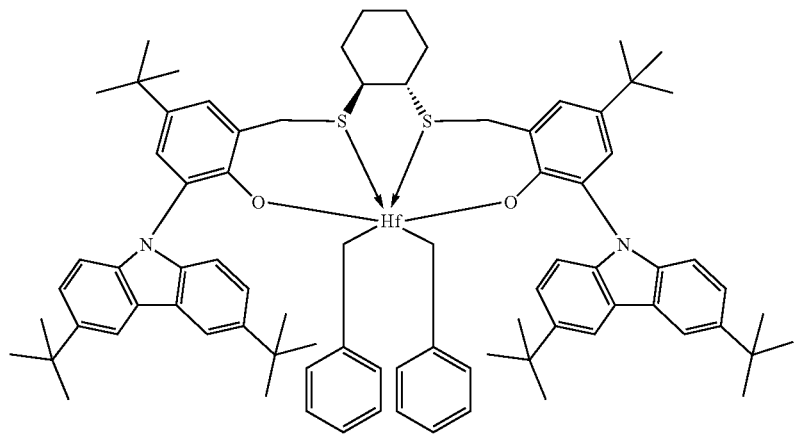
Catalyst 2
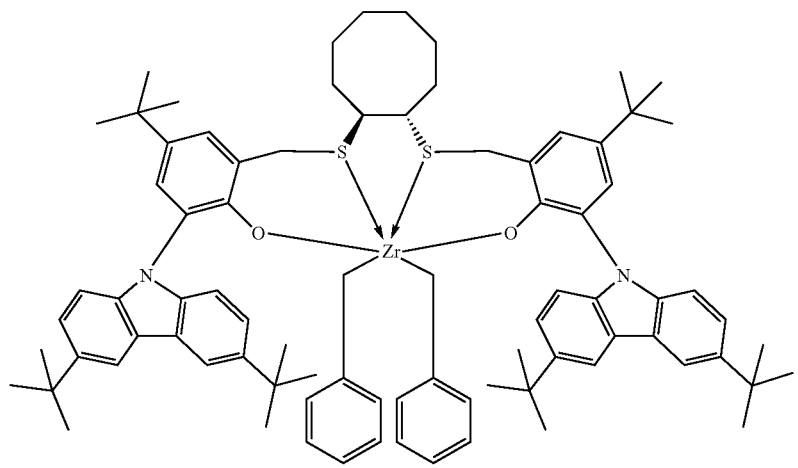
Catalyst 3

-continued

Catalyst 4

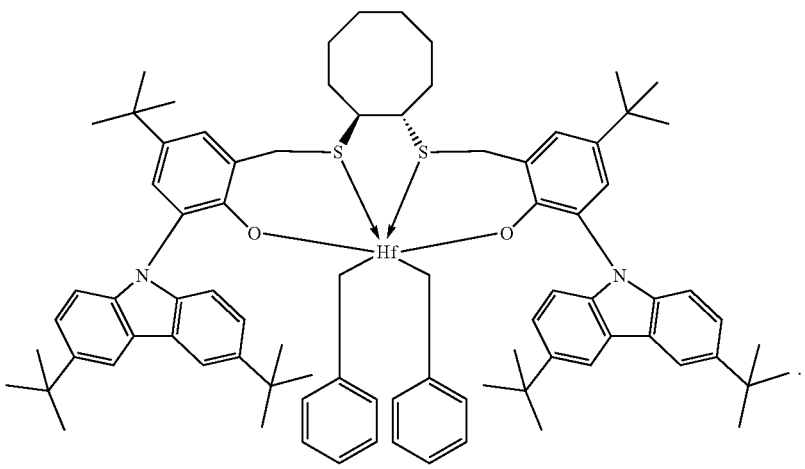

Useful catalyst compounds described above can readily be prepared by means in the art, such as those shown in the Experimental section below.

Activators

The terms "cocatalyst" and "activator" are used herein interchangeably and are defined to be any compound which can activate any one of the catalyst compounds described above by converting the neutral catalyst compound to a catalytically active catalyst compound cation.

After the complexes described above have been synthesized, catalyst systems may be formed by combining them with activators in any manner known from the literature including by supporting them for use in slurry or gas phase polymerization. The catalyst systems may also be added to or generated in solution polymerization or bulk polymerization (in the monomer). The catalyst system typically comprise a complex as described above and an activator such as alumoxane or a non-coordinating anion.

A preferred genus of activator is the noncoordinating anion (NCA), which is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator, and stoichiometric ionic activator can be used interchangeably. Likewise, the terms neutral stoichiometric activator, and Lewis acid activator can be used interchangeably. The term non-coordinating anion includes neutral stoichiometric activators, ionic stoichiometric activators, ionic activators, and Lewis acid activators.

"Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri (n-butyl) ammonium tetrakis (pentafluorophenyl) borate, tris perfluorophenyl boron metalloid precursor or tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

The catalyst systems of this invention can include at least one non-coordinating anion (NCA) activator.

In a preferred embodiment, boron containing NCA activators represented by the formula below can be used:

$$Z_d^+(A^{d-})$$

where: Z is (L-H) or a reducible Lewis acid; L is a neutral Lewis base; H is hydrogen; (L-H) is a Bronsted acid; $A^{d-}$ is a boron containing non-coordinating anion having the charge d−; d is 1, 2, or 3.

The cation component, $Z_d^+$ may include Bronsted acids such as protons or protonated Lewis bases or reducible Lewis acids capable of protonating or abstracting a moiety, such as an alkyl or aryl, from the transition metal catalyst precursor, resulting in a cationic transition metal species.

The activating cation $Z_d^+$ may also be a moiety such as silver, tropylium, carboniums, ferroceniums and mixtures, preferably carboniums and ferroceniums. Most preferably $Z_d^+$ is triphenyl carbonium. Preferred reducible Lewis acids can be any triaryl carbonium (where the aryl can be substituted or unsubstituted, such as those represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl), preferably the reducible Lewis acids in formula (14) above as "Z" include those represented by the formula: (Ph₃C), where Ph is a substituted or unsubstituted phenyl, preferably substituted with $C_1$ to $C_{40}$ hydrocarbyls or substituted a $C_1$ to $C_{40}$ hydrocarbyls, preferably $C_1$ to $C_{20}$ alkyls or aromatics or substituted $C_1$ to $C_{20}$ alkyls or aromatics, preferably Z is a triphenylcarbonium.

When $Z_d^+$ is the activating cation $(L-H)_d^+$, it is preferably a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, bis(hydrogenatedtallow)methylamine and related long-chain alkylamines, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers such as dimethyl ether diethyl ether, tetrahydrofuran and dioxane, sulfoniums from thioethers, such as diethyl thioethers, tetrahydrothiophene, and mixtures thereof.

The anion component $A^{d-}$ includes those having the formula $[M^{k+}Q_n]^{d-}$ wherein k is 1, 2, or 3; n is 1, 2, 3, 4, 5, or 6 (preferably 1, 2, 3, or 4); n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting, examples of boron compounds which may be used as an activating cocatalyst are the compounds described as (and particularly those specifically listed as) activators in U.S. Pat. No. 8,658,556, which is incorporated by reference herein.

Most preferably, the ionic stoichiometric activator $Z_d^+$ $(A^{d-})$ is one or more of N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetra(perfluorophenyl)borate, bis(hydrogenatedtallow)methylammonium tetrakis(perfluorophenyl)borate, or bis(hydrogenatedtallow)methylammonium tetrakis(perfluoronaphthyl)borate.

Bulky activators are also useful herein as NCAs. "Bulky activator" as used herein refers to anionic activators represented by the formula:

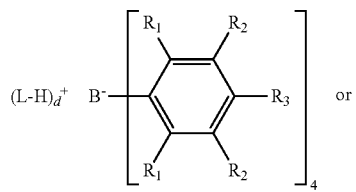

or

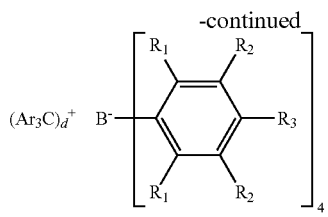

where:

each $R_1$ is, independently, a halide, preferably a fluoride;

Ar is substituted or unsubstituted aryl group (preferably a substituted or unsubstituted phenyl), preferably substituted with $C_1$ to $C_{40}$ hydrocarbyls, preferably $C_1$ to $C_{20}$ alkyls or aromatics;

each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_2$ is a fluoride or a perfluorinated phenyl group);

each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring); and L is a neutral Lewis base; $(L-H)^+$ is a Bronsted acid; d is 1, 2, or 3;

wherein the anion has a molecular weight of greater than 1020 g/mol;

wherein at least three of the substituents on the B atom each have a molecular volume of greater than 250 cubic A, alternately greater than 300 cubic A, or alternately greater than 500 cubic A.

Preferably $(Ar_3C)_d^+$ is $(Ph_3C)_d^+$, where Ph is a substituted or unsubstituted phenyl, preferably substituted with $C_1$ to $C_{40}$ hydrocarbyls or substituted $C_1$ to $C_{40}$ hydrocarbyls, preferably $C_1$ to $C_{20}$ alkyls or aromatics or substituted $C_1$ to $C_{20}$ alkyls or aromatics.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple 'Back of the Envelope' Method for Estimating the Densities and Molecular Volumes of Liquids and Solids," Journal of Chemical Education, Vol. 71, No. 11, November 1994, pp. 962-964. Molecular volume (MV), in units of cubic A, is calculated using the formula: $MV=8.3V_s$, where $V_s$ is the scaled volume. $V_s$ is the sum of the relative volumes of the constituent atoms, and is calculated from the molecular formula of the substituent using the following table of relative volumes. For fused rings, the $V_s$ is decreased by 7.5% per fused ring.

| Element | Relative Volume |
| --- | --- |
| H | 1 |
| $1^{st}$ short period, Li to F | 2 |
| $2^{nd}$ short period, Na to Cl | 4 |
| $1^{st}$ long period, K to Br | 5 |
| $2^{nd}$ long period, Rb to I | 7.5 |
| $3^{rd}$ long period, Cs to Bi | 9 |

For a list of particularly useful Bulky activators, please see U.S. Pat. No. 8,658,556, which is incorporated by reference herein.

In another embodiment, one or more of the NCA activators is chosen from the activators described in U.S. Pat. No. 6,211,105.

Preferred activators include N,N-dimethylanilinium tetrakis(perfluoronaphthyl)borate, N,N-dimethylanilinium tetrakis(perfluorobiphenyl)borate, N,N-dimethylanilinium tetrakis(perfluorophenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, $[Ph_3C^+]$ $[B(C_6F_5)_4^-]$, $[Me_3NH^+][B(C_6F_5)_4^-]$; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyeborate, triphenylcarbenium tetrakis(perfluoronaphthyl) borate, triphenylcarbenium tetrakis(perfluorobiphenyl) borate, triphenylcarbenium tetrakis(3,5-bis(trifluoromethyl)phenyl)borate).

In another embodiment, the activator comprises one or more of bis(hydrogenatedtallow)methylammonium tetrakis (perfluorophenyl)borate, bis(hydrogenatedtallow)methylammonium tetrakis(perfluoronaphthyl)borate, trialkylammonium tetrakis(pentafluorophenyl)borate, N,N-dialkylanilinium tetrakis(pentafluorophenyl)borate, N,N-dimethyl-(2,4,6-trimethylanilinium) tetrakis(pentafluorophenyl)borate, trialkylammonium tetrakis-(2,3, 4,6-tetrafluorophenyl) borate, N,N-dialkylanilinium tetrakis-(2,3,4,6-tetrafluorophenyl)borate, trialkylammonium tetrakis(perfluoronaphthyl)borate, N,N-dialkylanilinium tetrakis(perfluoronaphthyl)borate, trialkylammonium tetrakis(perfluorobiphenyl)borate, N,N-dialkylanilinium tetrakis(perfluorobiphenyl)borate, trialkylammonium tetrakis(3,5-bis(trifluoromethyl)phenyl) borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl)phenyl)borate, di-(i-propyl) ammonium tetrakis(pentafluorophenyl)borate, (where alkyl is methyl, ethyl, propyl, n-butyl, sec-butyl, or t-butyl).

The typical activator-to-catalyst ratio, e.g., all NCA activators-to-catalyst ratio is about a 1:1 molar ratio. Alternately, preferred ranges include from 0.1:1 to 100:1, alternately from 0.5:1 to 200:1, alternately from 1:1 to 500:1 alternately from 1:1 to 1000:1. A particularly useful range is from 0.5:1 to 10:1, preferably 1:1 to 5:1.

It is also within the scope of this invention that the catalyst compounds can be combined with combinations of alumoxanes and NCA's (see for example, U.S. Pat. Nos. 5,153,157; 5,453,410; EP 0 573 120 B1; WO 94/07928; and WO 95/14044, which discuss the use of an alumoxane in combination with an ionizing activator).

Chain transfer agents can also be used herein. Useful chain transfer agents are typically alkylalumoxanes, a compound represented by the formula $AlR_3$, $ZnR_2$ (where each R is, independently, a $C_1$-$C_8$ aliphatic radical, preferably methyl, ethyl, propyl, butyl, pentyl, hexyl octyl or an isomer thereof) or a combination thereof, such as diethyl zinc, methylalumoxane, trimethylaluminum, triisobutylaluminum, trioctylaluminum, or a combination thereof.

Optional Scavengers or Co-Activators

In addition to these activator compounds, scavengers or co-activators may be used. Aluminum alkyl or organoaluminum compounds which may be utilized as scavengers or co-activators include, for example, trimethylaluminum, triethylaluminum, triisobutylaluminum, diisobutylaluminum hydride, tri-n-hexylaluminum, tri-n-octylaluminum, alkylalumoxane (such as methylalumoxane), modified methylalumoxane, and diethyl zinc. In some embodiments, the scavenger is present at a molar ratio to the catalyst at 160 or less, preferably 100 or less, more preferably at 50 or less. In some embodiments of the invention, no scavenger is used. Alternately, the scavenger may be present at molar ratios to the catalyst of from about 0 to 160, alternately, 0 to 80, alternately 0 to 40, alternately 0 to 20.

Oligomerization Process

In embodiments herein, the invention relates to an oligomerization process where at least one $C_{8+}$ non-aromatic, preferably linear, alpha-olefin is contacted with a catalyst system comprising an activator and at least one catalyst compound, as described above. The catalyst compound and activator may be combined in any order, and are combined typically prior to contacting with the monomer.

Olefins useful herein include substituted or unsubstituted, $C_8$ to $C_{30}$ non-aromatic alpha-olefins (preferably linear alpha-olefins), preferably $C_8$ to $C_{24}$ non-aromatic alpha-olefins (preferably linear alpha-olefins), preferably $C_{10}$ to $C_{20}$ non-aromatic alpha-olefins (preferably linear alpha-olefins), preferably $C_{10}$ to $C_{16}$ non-aromatic alpha-olefins (preferably linear alpha-olefins), preferably $C_{10}$ to $C_{14}$ non-aromatic alpha-olefins (preferably linear alpha-olefins), preferably $C_8$, $C_{10}$, $C_{12}$ and or $C_{14}$ linear alpha olefins. Examples of suitable linear olefins include 1-octene, 1-nonene, 1-decene, 1-undecene, 1-dodecene, 1-tridecene, 1-tetradecene, 1-pentadecene and 1-hexadecene. In some embodiments, mixtures of two or more $C_{8+}$ alpha-olefins (preferably linear alpha-olefins) can be employed in the present process, for example, mixtures $C_{12}$ and $C_{14}$ linear alpha-olefins, mixtures $C_{14}$ and $C_{16}$ linear alpha-olefins, mixtures of $C_{10}$, $C_{14}$ and $C_8$ linear alpha-olefins, mixtures of $C_{10}$, $C_{12}$, and $C_{14}$ linear alpha-olefins, and mixtures $C_{12}$, $C_{14}$ and $C_{16}$ linear alpha-olefins. Where mixtures of a first $C_{8+}$ olefin, a second $C_{8+}$ olefin and optionally further $C_{8+}$ olefins are employed, the mixtures can, for example contain a weight ratio from 0.01:1 to 100:1, such as 0.05:1 to 50:1, for example 0.1:1 to 10:1, such as 0.5:1 to 5:1, of the first $C_{8+}$ olefin to the second $C_{8+}$. In any such mixture of first and second $C_{8+}$ olefins, the mixture may also contain up to 5 wt %, such as up to 25% wt %, for example up to 50 wt %, such as up to 75 wt %, even up to 90 wt % of a third $C_{8+}$ olefin. Particularly preferred are mixtures of $C_{8+}$ linear alpha-olefins which contain in excess of 50 wt % of 1-tetradecene.

The feed to the present oligomerization process may contain ethylene in addition to one or more $C_{8+}$ alpha-olefins (preferably linear alpha-olefins), since ethylene is found to increase the activity of the catalyst system used herein. The amount of ethylene present in the feed is not closely controlled, but in some embodiments the ethylene comprises from 0.1 to 10 wt % of the total feed, preferably 0.1 to 5 wt %, preferably 0.5 to 3 wt %. When ethylene is used in addition to the $C_{8+}$ alpha-olefin, conversion is calculated based on the weight of the $C_{8+}$ alpha-olefin monomer entering the reactor and the weight of the $C_{8+}$ alpha-olefin oligomer with added ethylene units produced. Most typically, the $C_{8+}$ alpha-olefin oligomer is a mixture containing from 0, 1 2 or 3 added ethylene units.

Oligomerization processes of this invention can be carried out in any manner known in the art. Any homogeneous, bulk, solution, or slurry oligomerization process known in the art can be used. Such processes can be run in a batch, semi-batch, or continuous mode. Homogeneous processes are preferred. (A homogeneous oligomerization process is defined to be a process where at least 90 wt % of the product is soluble in the reaction media.) A bulk homogeneous process is particularly preferred. (A bulk process is defined to be a process where monomer concentration in all feeds to the reactor is 70 vol % or more.) Alternately, no solvent or diluent is present or added in the reaction medium (except for the small amounts used as the carrier for the catalyst system or other additives, or amounts typically found with the monomer). Suitable diluents/solvents for use in the present oligomerization process include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable solvents also include liquid olefins which may act as monomers or comonomers including ethylene, 1-octene, 1-decene, 1-dodecene, 1-tetradecene and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt % based upon the weight of the solvents.

The present oligomerization process can be run at any temperature and/or pressure suitable to obtain the desired oligomerized product. Typical temperatures and/or pressures include a temperature in the range of from about 70° C. to about 300° C., preferably about 80° C. to about 200° C., preferably about 85° C. to about 160° C., preferably from about 90° C. to about 150° C., preferably from about 100° C. to about 150° C., preferably from about 110° C. to about 150° C., alternately from 80 to 110° C.; and a pressure in the range of from about 0.35 MPa to about 10 MPa, preferably from about 0.45 MPa to about 6 MPa, or preferably from about 0.5 MPa to about 4 MPa.

In some embodiments, the oligomerization temperature is 80° C. to 150° C.

In some embodiments, the oligomerization temperature is 80° C. to 150° C., the monomer conversion is at least 30 wt %, and the dimer selectivity is at least 40 wt %.

In some embodiments, the oligomerization temperature is 90° C. to 150° C., the monomer conversion is at least 30 wt % and the dimer selectivity is at least 40 wt %.

In some embodiments, the oligomerization temperature is 80° C. to 150° C., the monomer conversion is at least 30 wt % and the % vinylidene is 90 mol % or greater.

In some embodiments, the oligomerization temperature is 90° C. to 150° C., the monomer conversion is at least 30 wt %, the dimer selectivity is at least 40 wt %, and the % vinylidene is at least 90 mol %.

In some embodiments, the monomer conversion is at least 10 wt %, alternately at least 20 wt %, alternately at least 30 wt %, alternately at least 40 wt %, alternately at least 50 wt %, alternately at least 60 wt %, alternately at least 70 wt %, alternately at least 80 wt %.

In some embodiments, the dimer selectivity is at least 30 wt %, alternately at least 35 wt %, alternately at least 40 wt %, alternately at least 45 wt %, alternately at least 50 wt %, alternately at least 60 wt %, alternately at least 70 wt %, alternately at least 80 wt %, alternately at least 90 wt %.

Unless otherwise indicated herein:

1) Monomer conversion is 100×[(weight of desired product exiting reactor)/(weight of monomer entering reactor)]. For example, monomer conversion to dimer is 100×[(weight of dimer exiting reactor)/(weight of monomer entering reactor)] and monomer conversion to oligomer is 100×[(weight of all oligomer exiting reactor)/(weight of monomer entering reactor)].

2) Monomer conversion for a mixed $C_{8+}$ feed is 100× [(weight of $C_{2Z+}$oligomer exiting reactor)/(weight of $C_{Z+}$ monomer entering reactor)], where z is the carbon number of the smallest $C_{8+}$ monomer.

3) Monomer conversion for a feed containing ethylene and $C_{8+}$ monomer is 100×[(weight of $C_{2+}$ z+oligomer exiting reactor)/(weight of $C_{Z+}$ monomer entering reactor)], where z is the carbon number of the smallest $C_{8+}$ monomer.

Unless otherwise indicated, selectivity is 100×[(weight of desired product exiting reactor)/(weight of all oligomer exiting reactor)]. For example, dimer selectivity is 100× [(weight of dimer exiting reactor)/(weight of all oligomer exiting reactor)].

For calculations involving oligomer produced, the weight of the oligomer is the weight after volatiles, solvent, diluent, and unreacted monomers have been removed.

In a typical oligomerization, the run time of the reaction is up to 300 minutes, preferably in the range of from about 5 to 250 minutes, or preferably from about 10 to 120 minutes, alternately 10 to 60 minutes.

In some embodiments, hydrogen is present in the polymerization reactor at a partial pressure of 0.001 to 50 psig (0.007 to 345 kPa), preferably from 0.01 to 25 psig (0.07 to 172 kPa), more preferably 0.1 to 10 psig (0.7 to 70 kPa).

In some embodiments of the invention, an aluminum alkyl, alkylalumoxane, or zinc alkyl is present. Preferred molar ratios of Al/M or Zn/M where M represents the molar amount of the pre-catalyst is from 0 to 250, preferably 0.1 to 160, alternately 0.5 to 100, alternately 1 to 20. In some preferred embodiments of the invention, no aluminum or zinc reagents are present.

Oligomerized Products

This invention also relates to compositions of matter produced by the methods described herein.

In a preferred embodiment, the oligomerized product of the present process comprises one or more alpha-olefin dimers of the formula:

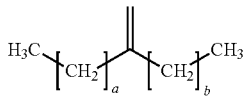

where "a" is an integer from 7-19 and "b" is an integer from 5-17, preferably "a" and "b" are odd numbered integers, preferably "a" is 7, 9, 11, 13, 15, 17, 19, or a mixture thereof, and "b" is 5, 7, 9, 11, 13, 15, 17, or a mixture thereof, preferably "a" is 7, 9, 13, or a mixture thereof and "b' is 5, 7, 11, or a mixture thereof, preferably "a" is 13 and "b" is 11. In some embodiments, a and b are the same, in other embodiments a and b are different.

Examples of dimers produced by the present process include 7-methylenepentadecane (dimer of 1-octene), 9-methylenenonadecane (dimer of 1-decene), 11-methylenetricosane (a dimer of 1-dodecene), 13-methyleneheptacosane (a dimer of 1-tetradecene), 15-methylenehentriacontane (a dimer of 1-hexadecene), or combinations of dimers of different $C_{8+}$ alpha-olefins.

In embodiments, the oligomerized product of the present process comprises at least 20 wt %, such as at least 30 wt %, such as at least 40 wt %, such as at least 50 wt % dimers of one or more $C_{8+}$ non-aromatic alpha-olefins. Alternately, the oligomerized product of the present process comprises from 20 to 100 wt %, alternately 30 to 99 wt %, alternately 40 to 98 wt %, alternately 50 to 95 wt % dimers of one or more $C_{8+}$ non-aromatic alpha-olefins. In this respect, the term "oligomerized product" refers only to the portion of the process effluent that has undergone oligomerization and does not include any unconverted monomers or other feedstock components.

The dimers produced by the present process are useful as waxes, lubricant additives and basestocks, and as reactive feedstocks for the production of surfactants, detergents, and dispersants.

The oligomers (preferably dimers) produced herein may be hydrogenated and are preferably hydrogenated and used as basestocks for engine oils and the like.

In an embodiment, the product of the process according to the invention, comprising alpha-olefin oligomers (preferably dimers), is hydrogenated. In particular, the product is preferably treated to reduce heteroatom catalyst components to less than 600 ppm, and then contacted with hydrogen and a hydrogenation catalyst to produce a dimer having a bromine number (ASTM D 1159) less than 1.8. Usually, the bromine number is below 1.8. Lower bromine number is more desirable, as it indicates an improved thermal/oxidative stability. In a preferred embodiment, the treated oligomer (preferably dimer) comprises 100 ppm of heteroatom catalyst components or less, preferably 10 ppm of heteroatom catalyst components or less. Preferably, the hydrogenation catalyst is selected from the group consisting of supported Group 7, 8, 9, and 10 metals, preferably the hydrogenation catalyst selected from the group consisting of one or more of Ni, Pd, Pt, Co, Rh, Fe, Ru, Os, Cr, Mo, and W, supported on silica, alumina, clay, titania, zirconia, or mixed metal oxide supports. A preferred hydrogenation catalyst is nickel supported on kieselguhr, or platinum or palladium supported on alumina, or cobalt-molybdenum supported on alumina. Usually, a high nickel content catalyst, such as 60% Ni on Kieselguhr catalyst is used, or a supported catalyst with high amount of Co—Mo loading. In a preferred embodiment, the oligomer (preferably dimer) product is contacted with hydrogen and a hydrogenation catalyst at a temperature from 25° C. to 350° C., preferably 100° C. to 300° C. In another preferred embodiment, the oligomer (preferably dimer) is contacted with hydrogen and a hydrogenation catalyst for a time period from 5 minutes to 100 hours, preferably from 5 minutes to 24 hours. In another preferred embodiment, the dimer is contacted with hydrogen and a hydrogenation catalyst at a hydrogen pressure of from 25 psi to 2500 psi, preferably from 100 to 2000 psi. In another preferred embodiment, the hydrogenation process reduces the number of mm triad groups in the oligomer (preferably dimer) by 1 to 80%. Hydrogenation of alpha olefin materials per se is well-known. See, for instance, U.S. Pat. No. 5,573,657 and "Lubricant Base Oil Hydrogen Refining Processes" in Lubricant Base Oil and Wax Processing, by Avilino Sequeira, Jr., Marcel Dekker, Inc., NY, 1994, pp. 119-152. The hydrogenation process can be accomplished in a slurry reactor in a batch operation or in a continuous stirred tank reactor (CSTR), where the catalyst concentration is 0.001 wt % to 20 wt % of the oligomer (preferably dimer) product, or preferably 0.01 wt % to 10 wt % of the product. Hydrogen and feed are added continuously to the reactor to allow for a certain residence time, usually 5 minutes to 10 hours, to allow complete hydrogenation of the unsaturated olefins and to allow proper conversion. The amount of catalyst added is usually in slight excess, to compensate for the catalyst deactivation. The catalyst and hydrogenated oligomer (preferably dimer) are continuously withdrawn from the reactor. The product mixture is then filtered, centrifuged or settled to remove the solid hydrogenation catalyst. The catalyst can be regenerated and reused. The hydrogenated oligomer (preferably dimer) can be used as is or further distilled or fractionated to the right component if necessary. In some cases, when the hydrogenation catalyst show no catalyst deactivation over long term operation, the stir tank hydrogenation process can be carried out in a manner where a fixed amount of catalyst is maintained in the reactor, usually 0.1 wt % to 10 wt % of the total reactant, and only hydrogen and dimer feed are continuously added at certain feed rate and only hydrogenated oligomer (preferably dimer) is withdrawn from the reactor. The hydrogenation process can also be accomplished by a fixed bed process, in which the solid catalyst is packed inside a tubular reactor and heated to reactor temperature. Hydrogen and oligomer (preferably dimer) feed can be fed through the reactor simultaneously from the top or bottom or counter-currently to maximize the contact between hydrogen, oligomer (preferably dimer) and catalyst, and to allow best heat management. The feed rate of the oligomer (preferably dimer) and hydrogen are adjusted to give proper residence to allow complete hydrogenation of the unsaturated olefins in the feed and to allow desirable conversion of mm triads in the process. The hydrogenated oligomer (preferably dimer) fluid can be used as is or further distilled or fractionated to give the desired component, if necessary.

In some embodiments, the functionalized (i.e., vinylidene containing) oligomers (preferably dimers) produced herein are further functionalized (derivatized), such as described in U.S. Pat. No. 6,022,929; A. Toyota, T. Tsutsui, and N. Kashiwa, Polymer Bulletin 48, pp. 213-219, 2002; J. Am. Chem. Soc., 1990, 112, pp. 7433-7434; and WO 2009/155472.

The functionalized and or derivatized oligomer (preferably dimer) materials may be used in oil additivation, lubricants, fuels and many other applications. Preferred uses include additives for lubricants and or fuels. The functionalized oligomers (preferably dimers) and/or derivatized oligomers (preferably dimers) produced herein have uses as lubricating additives which can act as dispersants, viscosity index improvers, or multifunctional viscosity index improvers. Additionally, they may be used as disinfectants (functionalized amines) and or wetting agents.

The functionalized oligomers (preferably dimers) and/or derivatized oligomers (preferably dimers) described herein may be combined with other additives (such as viscosity index improvers, corrosion inhibitor, oxidation inhibitor, dispersant, lube oil flow improver, detergents, demulsifiers, rust inhibitors, pour point depressant, anti-foaming agents, antiwear agents, seal swellant, friction modifiers, and the like (described for example in U.S. Pat. No. 6,022,929 at columns 60, line 42-column 78, line 54 and the references cited therein) to form compositions for many applications, including but not limited to lube oil additive packages, lube oils, and the like. Compositions containing these additives are typically are blended into a base oil in amounts which are effective to provide their normal attendant function. Representative effective amounts of such additives are illustrated as follows:

| Compositions | (Typical) wt %* | (Preferred) wt %* |
|---|---|---|
| V.I. Improver | 1-12 | 1-4 |
| Corrosion Inhibitor | 0.01-3 | 0.01-1.5 |
| Oxidation Inhibitor | 0.01-5 | 0.01-1.5 |
| Dispersant | 0.1-10 | 0.1-5 |
| Lube Oil Flow Improver | 0.01-2 | 0.01-1.5 |
| Detergents and Rust inhibitors | 0.01-6 | 0.01-3 |
| Pour Point Depressant | 0.01-1.5 | 0.01-1.5 |
| Anti-Foaming Agents | 0.001-0.1 | 0.001-0.01 |
| Antiwear Agents | 0.001-5 | 0.001-1.5 |
| Seal Swellant | 0.1-8 | 0.1-4 |
| Friction Modifiers | 0.01-3 | 0.01-1.5 |
| Lubricating Base Oil | Balance | Balance |

*Wt %'s are based on active ingredient content of the additive, and/or upon the total weight of any additive-package, or formulation which will be the sum of the A.I. weight of each additive plus the weight of total oil or diluent.

When other additives are employed, it may be desirable, although not necessary, to prepare additive concentrates comprising concentrated solutions or dispersions of the subject additives of this invention (in concentrate amounts hereinabove described), together with one or more of said other additives (said concentrate when constituting an additive mixture being referred to herein as an additive-package) whereby several additives can be added simultaneously to the base oil to form the lubricating oil composition. Dissolution of the additive concentrate into the lubricating oil may be facilitated by solvents and by mixing accompanied with mild heating, but this is not essential. The subject functionalized or derivatized oligomers (preferably dimers) of the present invention can be added to small amounts of base oil or other compatible solvents along with other desirable additives to form additive-packages containing active ingredients in collective amounts of typically from about 2.5% to about 90%, and preferably from about 15% to about 75%, and most preferably from about 25% to about 60% by weight additives in the appropriate proportions with the remainder being base oil.

The final formulations may employ typically about 10 wt % of the additive-package with the remainder being base oil.

In another embodiment, the dimers described herein can be used in any process, blend or product disclosed in WO 2009/155472 or U.S. Pat. No. 6,022,929, which are incorporated by reference herein.

In a preferred embodiment, this invention relates to a fuel comprising any oligomer (preferably dimer) produced herein. In a preferred embodiment, this invention relates to a lubricant comprising any oligomer (preferably dimer) produced herein.

The invention will now be more particularly described with reference to the following non-limiting Examples.

Ligand and Catalyst Syntheses

Synthesis of Ligand-A (Lig-A)

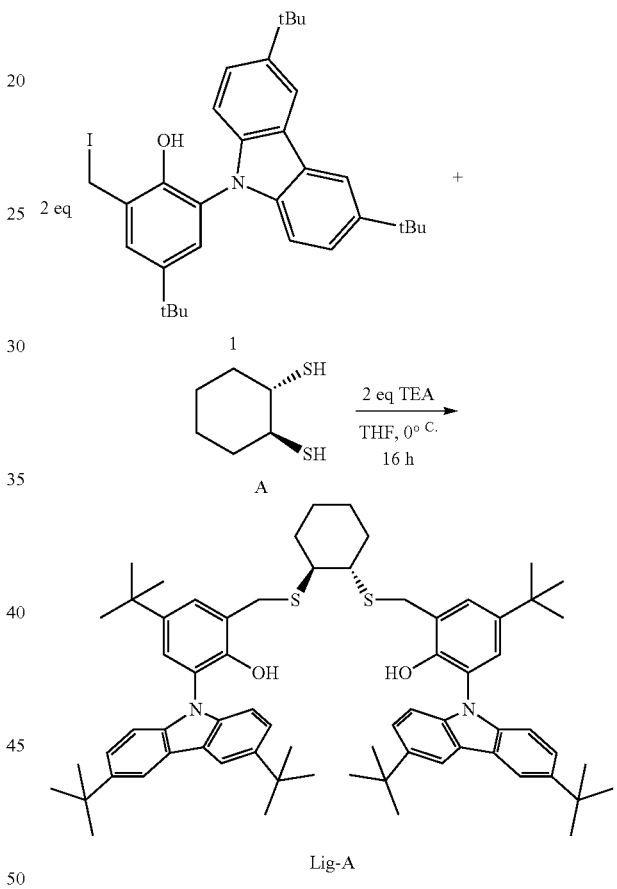

A 100 mL round bottom flask was charged with 1 (2.034 g, 3.58 mmol) and 30 mL tetrahydrofuran (THF) and the resulting solution was cooled to 0° C. In a separate vial, (1S,2S)-cyclohexane-1,2-dithiol (A) (0.266 g, 1.79 mmol) was dissolved in 5 mL THF and added to the cooled flask. Triethylamine (TEA) (0.5 mL, 3.58 mmol) was then added and the reaction was allowed to stir for 16 h. The resulting mixture was filtered to remove the white precipitate and the filtrate was concentrated into an orange residue. Analysis of the crude product by thin layer chromatography (TLC) showed no residual starting material. The orange residue was dissolved in methylene chloride and washed with water (3×50 mL) and brine (1×50 mL). The combined organics were dried over MgSO$_4$, filtered and concentrated in vacuo. Yield of Lig-A (orange solid)=1.756 g (95%).

Synthesis of Catalyst 1

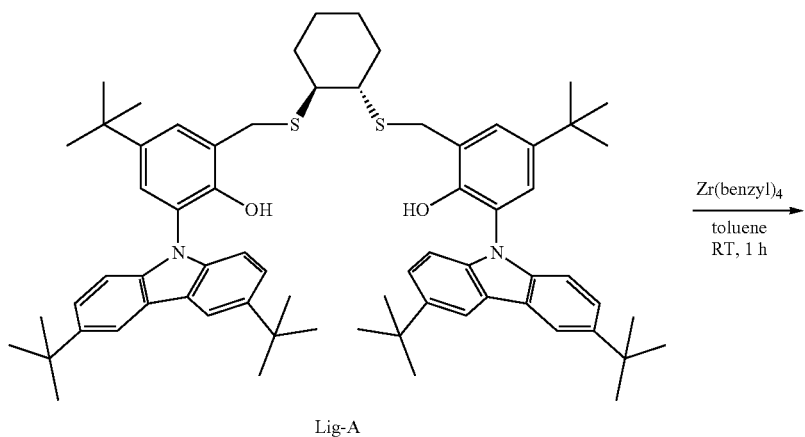

Lig-A

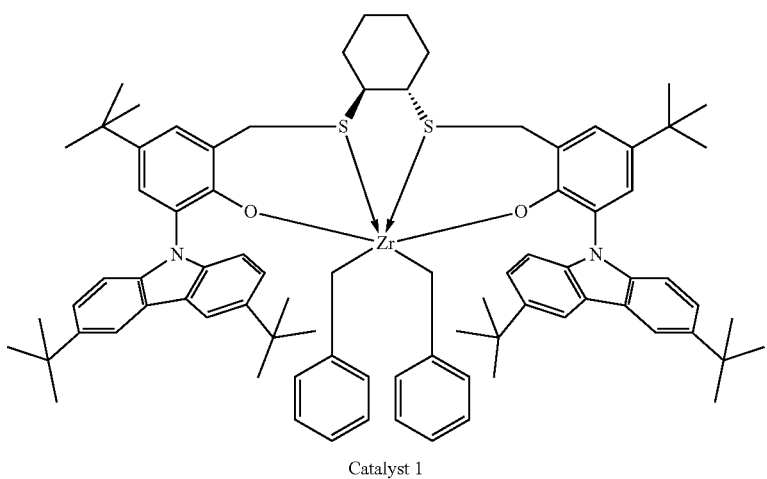

Catalyst 1

In two separate vials, Lig-A (0.463 g, 0.45 mmol) and Zr(benzyl)$_4$ (0.204 g, 0.45 mmol) were each dissolved in 5 mL of toluene. The zirconium solution was added to the ligand solution while stirring and the reaction was allowed to stir for 1 h. The reaction was concentrated, and the resulting yellow-orange residue was slurried in pentane then filtered to afford a yellow solid identified as Catalyst 1. Yield=0.187 g (32%).

Synthesis of Catalyst 2

Catalyst 2 is the hafnium complex of Lig-A and produced in the same way as Catalyst 1 but substituting Hf(benzyl)$_4$ for Zr(benzyl)$_4$.

Synthesis of Ligand-B (Lig-B)

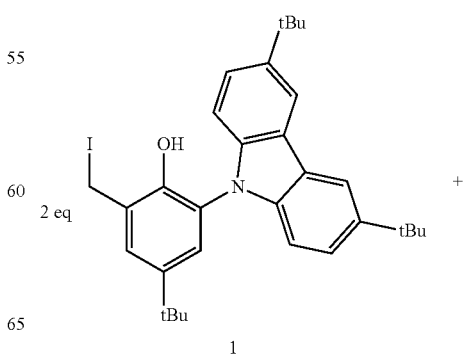

1

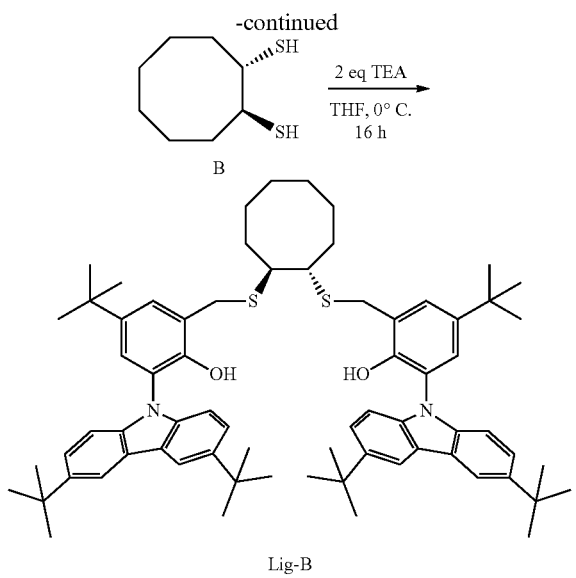

Lig-B

A 100 mL round bottom flask was charged with 1 (1.627 g, 2.87 mmol) and 30 mL of THF and the resulting solution was cooled to 0° C. In a separate vial, (1S,2S)-cyclooctane-1,2-dithiol (B) (0.253 g, 1.43 mmol) was dissolved in 5 mL of THF and added to the cooled flask. TEA (0.5 mL, 3.58 mmol) was then added and the reaction was allowed to stir for 16 h. The resulting mixture was filtered to remove the white precipitate and the filtrate was concentrated into an orange residue. TLC analysis showed multiple compounds in the crude product. The orange residue was dissolved in methylene chloride and washed with water (3×50 mL) and brine (1×50 mL). The combined organics were dried over $MgSO_4$, filtered and concentrated in vacuo. The resulting solid was purified on silica column using a 20%-100% $CH_2Cl_2$/hexane gradient. The product fraction was concentrated into an orange solid identified as Lig-B. Yield=0.429 g (29%).

Synthesis of Catalyst 3

Catalyst 3 is the zirconium complex of Lig-B and produced in the same way as Catalyst 1 but substituting Lig-B for Lig-A.

Synthesis of Catalyst 4

Catalyst 4 is the hafnium complex of Lig-B and produced in the same way as Catalyst 1 but substituting Lig-B for Lig-A and Hf(benzyl)$_4$ for Zr(benzyl)$_4$.

Oligomerization Examples

General Oligomerization Procedures for Parallel Pressure Reactor.

Solvents, polymerization-grade toluene, and isohexane were supplied by ExxonMobil Chemical Company and purified by passing through a series of columns two 500 cc Oxyclear cylinders in series from Labclear (Oakland, Calif.), followed by two 500 cc columns in series packed with dried 3 Å mole sieves (8-12 mesh; Aldrich Chemical Company), and two 500 cc columns in series packed with dried 5 Å mole sieves (8-12 mesh; Aldrich Chemical Company).

1-octene (O), 1-decene (D) and 1-tetradecene (TD) (98%, Aldrich Chemical Company) were dried by stirring over NaK overnight followed by filtration through basic alumina (Aldrich Chemical Company, Brockman Basic 1).

Polymerization-grade ethylene (C2) was used and further purified by passing the gas through a series of columns: 500 cc Oxyclear cylinder from Labclear (Oakland, Calif.) followed by a 500 cc column packed with dried 3A mole sieves (8-12 mesh; Aldrich Chemical Company) and a 500 cc column packed with dried 5A mole sieves (8-12 mesh; Aldrich Chemical Company).

Solutions of the metal complexes and activators were prepared in a drybox using toluene (anhydrous, stored under nitrogen; 98%). Concentrations were typically 0.5 to 5 mmol/L for the metal complexes and N,N-dimethylanilinium tetrakis-pentafluorophenyl borate (Activator-1) and 0.5% w/w for methyl alumoxane (MAO).

For oligomerization experiments with Activator-1 as activator, tri-n-octylaluminum (TNOAL, neat, AkzoNobel) was used as a scavenger. Concentration of the TNOAL solution in toluene ranged from 10 to 100 mmol/L.

Oligomerization experiments were carried out in a parallel, pressure reactor, as generally described in U.S. Pat. Nos. 6,306,658; 6,455,316; 6,489,168; WO 00/09255; and Murphy et al., J. Am. Chem. Soc., 2003, 125, pp. 4306-4317, each of which is fully incorporated herein by reference. The experiments were conducted in an inert atmosphere ($N_2$) drybox using autoclaves equipped with an external heater for temperature control, glass inserts (internal volume of reactor=23.5 mLs), septum inlets, regulated supply of nitrogen, ethylene and propylene, and equipped with disposable PEEK mechanical stirrers (800 RPM). The autoclaves were prepared by purging with dry nitrogen at 150° C. for 5 hours and then at 25° C. for 5 hours. Although the specific quantities, temperatures, solvents, reactants, reactant ratios, pressures, and other variables are frequently changed from one oligomerization run to the next, the following describes a typical oligomerization performed in a parallel, pressure reactor.

Catalyst systems dissolved in solution were used in the oligomerization examples below, unless specified otherwise.

Higher Alpha-Olefin Oligomerization.

A pre-weighed glass vial insert and disposable stirring paddle were fitted to each reaction vessel of the reactor, which contains 48 individual reaction vessels. The reactor was then closed and purged with nitrogen. Each vessel was charged with enough solvent (either isohexane or decane) to bring the total reaction volume, including the subsequent additions, to the desired volume, typically 5 mL. The monomer (typically 1-octene (O), 1-decene (D), or 1-tetradecene (TD)) was injected into the reaction vessel and the reactor was heated to the set temperature and stirred at 800 rpm. The vessels were then pressurized with nitrogen (typically 80 psi), and then the TNOAL in toluene was injected as scavenger followed by addition of the activator solution (typically 1.0-1.2 molar equivalents of N,N-dimethylanilinium tetrakis-pentafluorophenyl borate-Activator-1).

The catalyst solution (typically 0.04-1.2 umol of metal complex) was injected into the reaction vessel and the oligomerization was allowed to proceed for a set amount of time (maximum reaction time typically 120 minutes). The reaction was quenched by pressurizing the vessel with compressed air. After the reactor was vented and cooled, the glass vial insert containing the product, unreacted monomer and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the estimated yield of the product and the estimated conversion of the monomer. The resultant product was analyzed by GC-FID (see below) to determine the composition, and by $^1$H NMR spectroscopy (see below) to determine vinylidene content which was not corrected for residual starting material. For these examples, the product yield and monomer conversion were corrected using the wt % unreacted monomer from the GC-FID analysis of the product samples.

Estimated conversion (est C8+ alpha-olefin cony (%)) is 100 times the weight of the isolated sample (which includes some unreacted alpha-olefin) divided by the weight of the $C_{8+}$ alpha-olefin added to the reactor.

Estimated activity (est activity (g pdt/mmol cat-h)) is calculated from the mass of isolated sample ("pdt", which includes some unreacted alpha-olefin) divided by the mmol of catalyst used and the time in hours.

Corrected yield is calculated by multiplying the mass of the isolated sample by the total fraction of the desired oligomers (e.g., dimers, trimers, tetramers, pentamer, etc) in the isolated sample based on the GC Analysis.

Corrected conversion is calculated by multiplying the estimated conversion by the total fraction of the dimers, trimers, tetramers, and pentamers in the isolated sample based from the GC Analysis. Selectivity for the dimer is calculated based on the mass of the dimer divided by the total mass of the dimer, trimer, tetramers pentamers.

Corrected activity is calculated by multiplying the estimated activity by the total fraction of the desired oligomers (e.g., dimers, trimers, tetramers, pentamers, etc.) in the isolated sample based on the GC Analysis.

Tetradecene oligomerization reactions are recorded in Tables 1 and 2. Decene oligomerization reactions and octene oligomerization reactions are reported in Table 4.

Tetradecene (TD) Oligomerization in the Presence of Ethylene.

The reactor was prepared as described above and purged with ethylene. Each vessel was charged with enough solvent (either isohexane or decane) to bring the total reaction volume, including the subsequent additions, to the desired volume, typically 5 mL. Tetradecene (C14) was injected into the reaction vessel and the reactor was heated to the set temperature and stirred at 800 rpm. The vessels were then pressurized with nitrogen (typically 80 psi), followed by a specified fixed amount of ethylene (typically 10 psi, no continuous feed). The scavenger and/or chain transfer agent, activator (typically Activator-1) and catalyst solutions were injected sequentially to each vessel and the oligomerization was allowed to proceed as described previously. Tetradecene oligomerization reactions including some in the presence of ethylene are reported in Table 3.

Product Characterization

Figure 2:
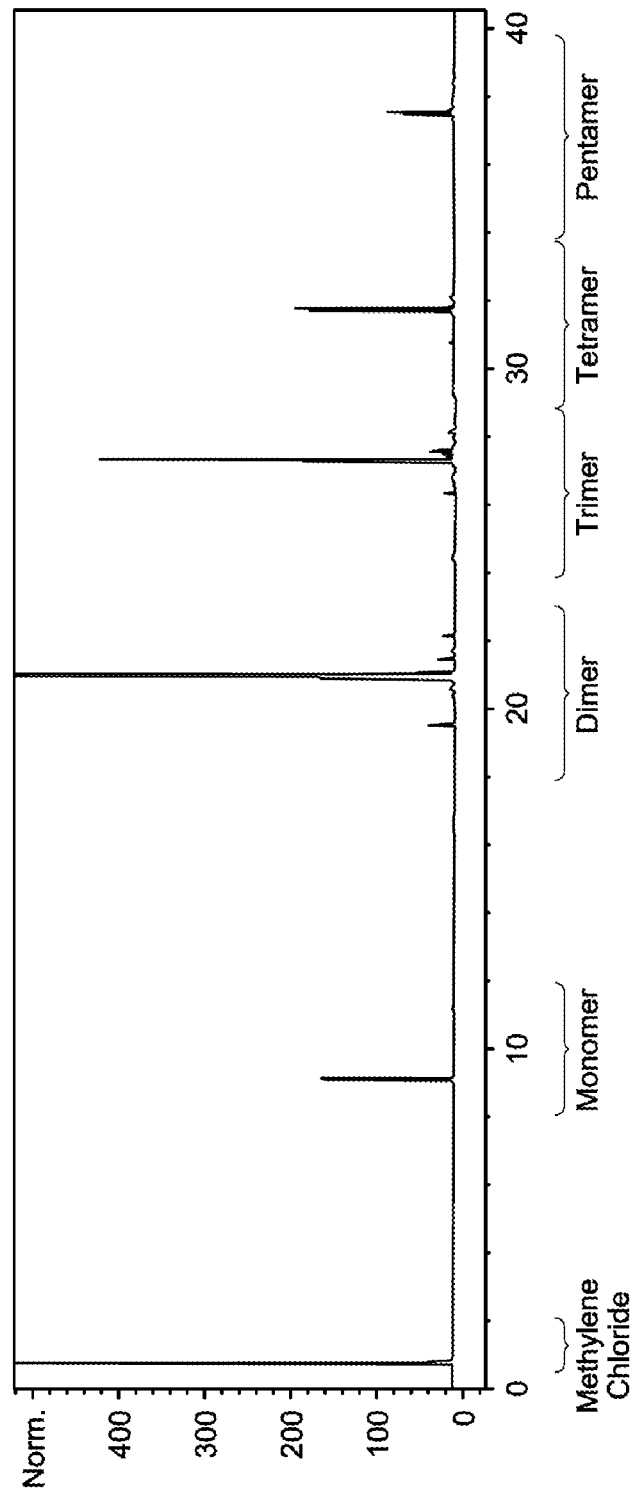
FIG. 2 is a gas chromatogram of the oligomerized product obtained in Table 3, Experiment 3-6, made from a combination of 1-tetradecene and ethylene.
Figure 3:
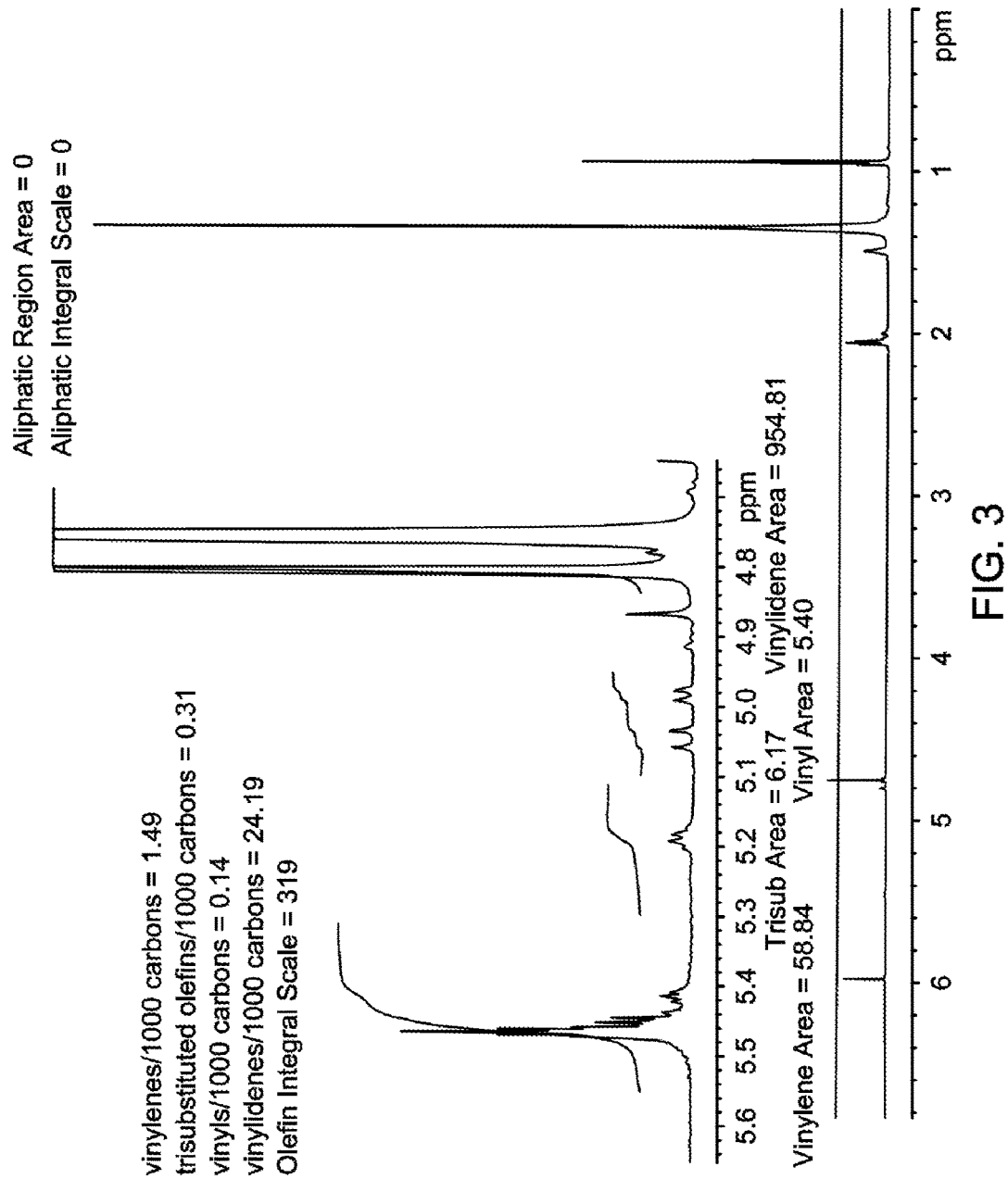
FIG. 3 is a proton NMR spectrum of the oligomerized product obtained in Experiment 2-2, Table 2, and Table 5.

To determine the composition of the product mixture, the samples were analyzed by gas chromatography using an Agilent 6890 GC, equipped with FID, on a DB-1HT type 0.25 mm*15 m*0.10 um dimethyl siloxane column with a He carrier gas. The sample was diluted with methylene chloride to <1 wt %. The temperature was ramped from 40° C. to 390° C. over 55 minutes. The GC peaks were integrated within the approximate following time range (in minutes): See FIGS. 1 and 2 for examples of peak assignment:

| Monomer | 9-11 |
| Dimer | 18-23 |
| Trimer | 24-29 |
| Tetramer | 29-34 |
| Pentamer | 34-40 |

GC data for select samples are reported in Tables 1, 2 and 3. Wt. % of unreacted monomer, wt. % dimer, wt. % trimer, wt. % tetramer, wt. % pentamer are calculated from the peak integral (assignments above) multiplied by 100 and divided by the sum of the integrals for the wt. % of unreacted monomer, wt. % dimer, wt. % trimer, wt. % tetramer, and wt. % pentamer.

$^1$H NMR data were collected at 120° C. in a 5 or 10 mm probe using a spectrometer with a $^1$H frequency of at least 500 MHz (for purposes of the claims 5 mm and 500 MHz are used). Data was recorded using a maximum pulse width of 45°, 5 seconds between pulses and signal averaging 512 transients. Spectral signals were integrated. Samples were dissolved in deuterated 1,1,2,2,-tetrachloroethane at concentrations of 1-2 wt % prior to being inserted into the spectrometer magnet. Prior to data analysis, spectra were referenced by setting the residual hydrogen-containing solvent resonance to 5.98 ppm. Vinylene unsaturations (two protons) were measured as the number of vinylenes per 1000 carbon atoms using the resonances between 5.55-5.31 ppm. Trisubstituted unsaturations ("trisubs"; one proton) were measured as the number of trisubstituted groups per 1000 carbon atoms using the resonances between 5.30-5.11 ppm. Vinyl unsaturations (two protons) were measured as the number of vinyls per 1000 carbon atoms using the resonances between 5.10-4.95 ppm. Vinylidene unsaturations (2 protons) were measured as the number of vinylidenes per 1000 carbon atoms using the resonances between 4.84-4.70 ppm. Vinylidene unsaturations are reported as a molar percentage of the total number of moles of unsaturated groups (that is, the sum of vinyl, vinylidene, vinylene, and trisubstituted unsaturations). Unsaturation data for select samples are reported in Table 5.

Oligomerization Examples

TABLE 1

TD oligomerization at varying temperatures and reaction times.

| Expt | T (° C.) | actual quench time (s) | mass of isolated sample (g) | Est activity (g pdt/mmol cat-h) | Est TD conv (%) | wt % unreacted monomer (GC) | wt % dimer (GC) | wt % trimer (GC) |
|---|---|---|---|---|---|---|---|---|
| 1 | 80 | 300 | 0.047 | 4680 | 6.0 | | | |
| 2 | 80 | 301 | 0.081 | 8103 | 10.5 | | | |
| 3 | 80 | 900 | 0.139 | 4633 | 17.9 | 7.4 | 46.6 | 19.0 |
| 4 | 80 | 900 | 0.135 | 4510 | 17.5 | | | |
| 5 | 80 | 1800 | 0.169 | 2820 | 21.8 | | | |
| 6 | 80 | 1801 | 0.161 | 2674 | 20.7 | | | |
| 7 | 80 | 3601 | 0.199 | 1661 | 25.7 | | | |

TABLE 1-continued

TD oligomerization at varying temperatures and reaction times.

| | | | | | | | | |
|---|---|---|---|---|---|---|---|---|
| 8 | 80 | 3601 | 0.192 | 1600 | 24.8 | | | |
| 9 | 80 | 5400 | 0.231 | 1283 | 29.8 | | | |
| 10 | 80 | 5401 | 0.212 | 1175 | 27.3 | | | |
| 11 | 80 | 7200 | 0.248 | 1035 | 32.1 | | | |
| 12 | 80 | 7200 | 0.227 | 944 | 29.2 | | | |
| 13 | 100 | 300 | 0.100 | 9980 | 12.9 | | | |
| 14 | 100 | 300 | 0.090 | 9040 | 11.7 | | | |
| 15 | 100 | 900 | 0.151 | 5027 | 19.5 | | | |
| 16 | 100 | 901 | 0.146 | 4861 | 18.8 | | | |
| 17 | 100 | 1800 | 0.184 | 3073 | 23.8 | | | |
| 18 | 100 | 1801 | 0.187 | 3115 | 24.1 | | | |
| 19 | 100 | 3600 | 0.242 | 2015 | 31.2 | | | |
| 20 | 100 | 3601 | 0.260 | 2164 | 33.5 | 5.2 | 49.3 | 21.0 |
| 21 | 100 | 5400 | 0.261 | 1449 | 33.7 | | | |
| 22 | 100 | 5401 | 0.276 | 1535 | 35.7 | | | |
| 23 | 100 | 7200 | 0.305 | 1273 | 39.4 | | | |
| 24 | 100 | 7200 | 0.290 | 1208 | 37.4 | | | |
| 25 | 110 | 301 | 0.101 | 10037 | 13.0 | | | |
| 26 | 110 | 301 | 0.094 | 9389 | 12.2 | | | |
| 27 | 110 | 900 | 0.154 | 5143 | 19.9 | | | |
| 28 | 110 | 901 | 0.157 | 5234 | 20.3 | | | |
| 29 | 110 | 1800 | 0.195 | 3242 | 25.1 | | | |
| 30 | 110 | 1801 | 0.199 | 3310 | 25.6 | | | |
| 31 | 110 | 3600 | 0.254 | 2115 | 32.7 | | | |
| 32 | 110 | 3601 | 0.265 | 2207 | 34.2 | | | |
| 33 | 110 | 5400 | 0.296 | 1642 | 38.1 | | | |
| 34 | 110 | 5401 | 0.312 | 1730 | 40.2 | | | |
| 35 | 110 | 7200 | 0.319 | 1328 | 41.1 | | | |
| 36 | 110 | 7201 | 0.343 | 1428 | 44.2 | 7.4 | 51.4 | 21.6 |

| Expt | wt % tetramer (GC) | wt % pentamer+ (GC) | Corrected Yield* (g) | Corrected activity* (g pdt/mmol cat-h) | Corrected TD conv* (%) | Selectivity for dimer (%) |
|---|---|---|---|---|---|---|
| 1 | | | | | | |
| 2 | | | | | | |
| 3 | 13.8 | 13.2 | 0.1287 | 4290 | 16.6 | 50.3 |
| 4 | | | | | | |
| 5 | | | | | | |
| 6 | | | | | | |
| 7 | | | | | | |
| 8 | | | | | | |
| 9 | | | | | | |
| 10 | | | | | | |
| 11 | | | | | | |
| 12 | | | | | | |
| 13 | | | | | | |
| 14 | | | | | | |
| 15 | | | | | | |
| 16 | | | | | | |
| 17 | | | | | | |
| 18 | | | | | | |
| 19 | | | | | | |
| 20 | 15.2 | 9.3 | 0.2462 | 2051 | 31.8 | 52.0 |
| 21 | | | | | | |
| 22 | | | | | | |
| 23 | | | | | | |
| 24 | | | | | | |
| 25 | | | | | | |
| 26 | | | | | | |
| 27 | | | | | | |
| 28 | | | | | | |
| 29 | | | | | | |
| 30 | | | | | | |
| 31 | | | | | | |
| 32 | | | | | | |
| 33 | | | | | | |
| 34 | | | | | | |
| 35 | | | | | | |
| 36 | 15.8 | 3.8 | 0.3173 | 1322 | 40.9 | 55.5 |

Conditions:
1 mL TD (0.775 g), 0.12 μmol Catalyst 1, 1.1 equiv Activator-1, 1.0 μmol TNOAL, 5 mL total volume, solvent = isohexane.
*Corrected values based on wt % unreacted monomer from GC analysis.

TABLE 2

Effect of TNOAL concentration on TD oligomerization.

| Expt | Catalyst-1 (umol) | TNOAL (umol) | T (° C.) | mass of isolated sample (g) | Est activity (g pdt/mmol cat-h) | Est TD conv (%) | wt % unreacted monomer (GC) | wt % dimer (GC) |
|---|---|---|---|---|---|---|---|---|
| 1 | 0.25 | 0.00 | 110 | 0.0976 | 195 | 12.6 | 0.2 | 58.46 |
| 2 | 0.25 | 0.00 | 110 | 0.0663 | 133 | 8.6 | | |
| 3 | 0.40 | 0.00 | 110 | 0.1755 | 219 | 22.6 | 0.3 | 60.2 |
| 4 | 0.40 | 0.00 | 110 | 0.1386 | 173 | 17.9 | | |
| 5 | 0.50 | 0.00 | 110 | 0.2066 | 207 | 26.7 | 0.3 | 53.9 |
| 6 | 0.50 | 0.00 | 110 | 0.1704 | 170 | 22.0 | | |
| 7 | 0.60 | 0.00 | 110 | 0.2188 | 182 | 28.2 | 0.4 | 59.4 |
| 8 | 0.60 | 0.00 | 110 | 0.1964 | 164 | 25.3 | | |
| 9 | 0.80 | 0.00 | 110 | 0.2675 | 167 | 34.5 | 0.5 | 59.8 |
| 10 | 0.80 | 0.00 | 110 | 0.2761 | 173 | 35.6 | | |
| 11 | 1.00 | 0.00 | 110 | 0.2795 | 140 | 36.1 | 0.3 | 60.7 |
| 12 | 1.00 | 0.00 | 110 | 0.3222 | 161 | 41.6 | | |
| 13 | 1.20 | 0.00 | 110 | 0.3024 | 126 | 39.0 | 0.4 | 61.0 |
| 14 | 1.20 | 0.00 | 110 | 0.3488 | 145 | 45.0 | | |
| 15 | 0.25 | 0.00 | 130 | 0.0283 | 57 | 3.7 | 0.3 | 57.7 |
| 16 | 0.25 | 0.00 | 130 | 0.0093 | 19 | 1.2 | | |
| 17 | 0.40 | 0.00 | 130 | 0.0513 | 64 | 6.6 | 0.3 | 58.3 |
| 18 | 0.40 | 0.00 | 130 | 0.0340 | 42 | 4.4 | | |
| 19 | 0.50 | 0.00 | 130 | 0.0829 | 83 | 10.7 | 0.3 | 59.2 |
| 20 | 0.50 | 0.00 | 130 | 0.0568 | 57 | 7.3 | | |
| 21 | 0.60 | 0.00 | 130 | 0.0820 | 68 | 10.6 | 0.5 | 58.6 |
| 22 | 0.60 | 0.00 | 130 | 0.0686 | 57 | 8.9 | | |
| 23 | 0.80 | 0.00 | 130 | 0.0853 | 53 | 11.0 | 0.4 | 59.8 |
| 24 | 0.80 | 0.00 | 130 | 0.0963 | 60 | 12.4 | | |
| 25 | 1.00 | 0.00 | 130 | 0.1460 | 73 | 18.8 | 0.5 | 60.7 |
| 26 | 1.00 | 0.00 | 130 | 0.1473 | 74 | 19.0 | | |
| 27 | 1.20 | 0.00 | 130 | 0.0982 | 41 | 12.7 | 0.5 | 60.7 |
| 28 | 1.20 | 0.00 | 130 | 0.1263 | 53 | 16.3 | | |
| 29 | 0.25 | 0.00 | 150 | 0.0225 | 45 | 2.9 | | |
| 30 | 0.25 | 0.00 | 150 | 0.0136 | 27 | 1.8 | | |
| 31 | 0.40 | 0.00 | 150 | 0.0192 | 24 | 2.5 | | |
| 32 | 0.40 | 0.00 | 150 | 0.0101 | 13 | 1.3 | | |
| 33 | 0.50 | 0.00 | 150 | 0.0080 | 8 | 1.0 | | |
| 34 | 0.50 | 0.00 | 150 | 0.0185 | 18 | 2.4 | | |
| 35 | 0.60 | 0.00 | 150 | 0.0082 | 7 | 1.1 | | |
| 36 | 0.60 | 0.00 | 150 | 0.0168 | 14 | 2.2 | | |
| 37 | 0.80 | 0.00 | 150 | 0.0135 | 8 | 1.7 | | |
| 38 | 0.80 | 0.00 | 150 | 0.0434 | 27 | 5.6 | | |
| 39 | 1.00 | 0.00 | 150 | 0.0149 | 7 | 1.9 | | |
| 40 | 1.00 | 0.00 | 150 | 0.0559 | 28 | 7.2 | | |
| 41 | 1.20 | 0.00 | 150 | 0.0172 | 7 | 2.2 | | |
| 42 | 1.20 | 0.00 | 150 | 0.0522 | 22 | 6.7 | | |
| 43 | 0.25 | 5 | 110 | 0.0894 | 179 | 11.5 | 6.5 | 37.7 |
| 44 | 0.25 | 5 | 110 | 0.1116 | 223 | 14.4 | | |
| 45 | 0.25 | 10 | 110 | 0.0396 | 79 | 5.1 | 2.8 | 41.0 |
| 46 | 0.25 | 10 | 110 | 0.0496 | 99 | 6.4 | | |
| 47 | 0.25 | 10 | 110 | 0.0273 | 55 | 3.5 | 0.1 | 59.7 |
| 48 | 0.25 | 10 | 110 | 0.0274 | 55 | 3.5 | | |
| 49 | 0.25 | 20 | 110 | 0.0254 | 51 | 3.3 | 0.2 | 54.4 |
| 50 | 0.25 | 20 | 110 | 0.0222 | 44 | 2.9 | | |
| 51 | 0.25 | 40 | 110 | 0.0189 | 38 | 2.4 | 0.2 | 55.9 |
| 52 | 0.25 | 40 | 110 | 0.0180 | 36 | 2.3 | | |
| 53 | 0.25 | 5 | 130 | 0.0443 | 89 | 5.7 | 2.1 | 37.8 |
| 54 | 0.25 | 5 | 130 | 0.0466 | 93 | 6.0 | | |
| 55 | 0.25 | 10 | 130 | 0.0165 | 33 | 2.1 | | |
| 56 | 0.25 | 10 | 130 | 0.0192 | 38 | 2.5 | | |
| 57 | 0.25 | 10 | 130 | 0.0289 | 58 | 3.7 | 0.2 | 60.3 |
| 58 | 0.25 | 10 | 130 | 0.0282 | 56 | 3.6 | | |
| 59 | 0.25 | 10 | 130 | 0.0086 | 17 | 1.1 | | |
| 60 | 0.25 | 10 | 130 | 0.0086 | 17 | 1.1 | | |
| 61 | 0.25 | 20 | 130 | 0.0116 | 23 | 1.5 | | |
| 62 | 0.25 | 20 | 130 | 0.0114 | 23 | 1.5 | | |
| 63 | 0.25 | 20 | 130 | 0.0132 | 26 | 1.7 | | |
| 64 | 0.25 | 20 | 130 | 0.0113 | 23 | 1.5 | | |
| 65 | 0.25 | 40 | 130 | 0.0126 | 25 | 1.6 | | |
| 66 | 0.25 | 40 | 130 | 0.0152 | 30 | 2.0 | | |
| 67 | 0.25 | 5 | 150 | 0.0412 | 82 | 5.3 | 0.1 | 50.0 |
| 68 | 0.25 | 5 | 150 | 0.0375 | 75 | 4.8 | | |
| 69 | 0.25 | 10 | 150 | 0.0255 | 51 | 3.3 | 0.8 | 62.0 |
| 70 | 0.25 | 10 | 150 | 0.0246 | 49 | 3.2 | | |
| 71 | 0.25 | 10 | 150 | 0.0357 | 71 | 4.6 | 1.2 | 78.9 |
| 72 | 0.25 | 10 | 150 | 0.0234 | 47 | 3.0 | | |
| 73 | 0.25 | 10 | 150 | 0.0264 | 53 | 3.4 | 1.0 | 78.9 |

TABLE 2-continued

Effect of TNOAL concentration on TD oligomerization.

| 74 | 0.25 | 10 | 150 | 0.0279 | 56 | 3.6 |  |  |
| 75 | 0.25 | 20 | 150 | 0.0259 | 52 | 3.3 | 0.8 | 84.9 |
| 76 | 0.25 | 20 | 150 | 0.0227 | 45 | 2.9 |  |  |
| 77 | 0.25 | 20 | 150 | 0.0217 | 43 | 2.8 | 1.1 | 71.3 |
| 78 | 0.25 | 20 | 150 | 0.0172 | 34 | 2.2 |  |  |
| 79 | 0.25 | 40 | 150 | 0.0258 | 52 | 3.3 | 0.57 | 88.8 |
| 80 | 0.25 | 40 | 150 | 0.0278 | 56 | 3.6 |  |  |
| 81 | 0.25 | 10 | 160 | 0.0375 | 75 | 4.8 | 1.55 | 77.3 |
| 82 | 0.25 | 10 | 160 | 0.0324 | 65 | 4.2 |  |  |
| 83 | 0.25 | 20 | 160 | 0.0377 | 75 | 4.9 | 1.70 | 83.2 |
| 84 | 0.25 | 20 | 160 | 0.0342 | 68 | 4.4 |  |  |

| Expt | wt % trimer (GC) | wt % tetramer (GC) | wt % pentamer+ (GC) | Corrected Yield* (g) | Corrected activity* (g pdt/mmol cat-h) | Corrected TD conv* (%) | Selectivity for dimer (%) |
|---|---|---|---|---|---|---|---|
| 1 | 23.0 | 11.9 | 6.5 | 0.0974 | 195 | 12.6 | 58.6 |
| 2 |  |  |  |  |  |  |  |
| 3 | 21.5 | 11.2 | 6.7 | 0.1749 | 219 | 22.6 | 60.4 |
| 4 |  |  |  |  |  |  |  |
| 5 | 24.2 | 15.0 | 6.6 | 0.2060 | 206 | 26.6 | 54.0 |
| 6 |  |  |  |  |  |  |  |
| 7 | 22.1 | 11.6 | 6.5 | 0.2180 | 182 | 28.1 | 59.6 |
| 8 |  |  |  |  |  |  |  |
| 9 | 21.8 | 11.4 | 6.5 | 0.2662 | 166 | 34.3 | 60.1 |
| 10 |  |  |  |  |  |  |  |
| 11 | 21.9 | 11.4 | 5.7 | 0.2785 | 139 | 35.9 | 60.9 |
| 12 |  |  |  |  |  |  |  |
| 13 | 22.2 | 10.8 | 5.7 | 0.3012 | 125 | 38.9 | 61.2 |
| 14 |  |  |  |  |  |  |  |
| 15 | 23.7 | 12.7 | 5.7 | 0.0282 | 56 | 3.6 | 57.8 |
| 16 |  |  |  |  |  |  |  |
| 17 | 22.9 | 11.8 | 6.7 | 0.0511 | 64 | 6.6 | 58.5 |
| 18 |  |  |  |  |  |  |  |
| 19 | 23.1 | 11.6 | 5.9 | 0.0827 | 83 | 10.7 | 59.3 |
| 20 |  |  |  |  |  |  |  |
| 21 | 23.1 | 11.4 | 6.5 | 0.0816 | 68 | 10.5 | 58.8 |
| 22 |  |  |  |  |  |  |  |
| 23 | 23.0 | 11.3 | 5.5 | 0.0850 | 53 | 11.0 | 60.0 |
| 24 |  |  |  |  |  |  |  |
| 25 | 22.0 | 10.9 | 5.9 | 0.1453 | 73 | 18.8 | 61.0 |
| 26 |  |  |  |  |  |  |  |
| 27 | 22.4 | 10.4 | 5.3 | 0.0977 | 41 | 12.6 | 61.5 |
| 28 |  |  |  |  |  |  |  |
| 29 |  |  |  |  |  |  |  |
| 30 |  |  |  |  |  |  |  |
| 31 |  |  |  |  |  |  |  |
| 32 |  |  |  |  |  |  |  |
| 33 |  |  |  |  |  |  |  |
| 34 |  |  |  |  |  |  |  |
| 35 |  |  |  |  |  |  |  |
| 36 |  |  |  |  |  |  |  |
| 37 |  |  |  |  |  |  |  |
| 38 |  |  |  |  |  |  |  |
| 39 |  |  |  |  |  |  |  |
| 40 |  |  |  |  |  |  |  |
| 41 |  |  |  |  |  |  |  |
| 42 |  |  |  |  |  |  |  |
| 43 | 21.3 | 24.7 | 9.9 | 0.0836 | 167 | 10.8 | 40.3 |
| 44 |  |  |  |  |  |  |  |
| 45 | 16.0 | 31.6 | 8.5 | 0.0385 | 77 | 5.0 | 42.2 |
| 46 |  |  |  |  |  |  |  |
| 47 | 21.8 | 13.0 | 5.4 | 0.0273 | 55 | 3.5 | 59.8 |
| 48 |  |  |  |  |  |  |  |
| 49 | 24.6 | 14.8 | 6.0 | 0.0253 | 51 | 3.3 | 54.5 |
| 50 |  |  |  |  |  |  |  |
| 51 | 20.7 | 19.6 | 3.7 | 0.0189 | 38 | 2.4 | 56.0 |
| 52 |  |  |  |  |  |  |  |
| 53 | 16.9 | 31.1 | 12.1 | 0.0434 | 87 | 5.6 | 38.6 |
| 54 |  |  |  |  |  |  |  |
| 55 |  |  |  |  |  |  |  |
| 56 |  |  |  |  |  |  |  |
| 57 | 23.4 | 10.9 | 5.2 | 0.0289 | 58 | 3.7 | 60.4 |
| 58 |  |  |  |  |  |  |  |
| 59 |  |  |  |  |  |  |  |
| 60 |  |  |  |  |  |  |  |
| 61 |  |  |  |  |  |  |  |

TABLE 2-continued

Effect of TNOAL concentration on TD oligomerization.

| | | | | | | | |
|---|---|---|---|---|---|---|---|
| 62 | | | | | | | |
| 63 | | | | | | | |
| 64 | | | | | | | |
| 65 | | | | | | | |
| 66 | | | | | | | |
| 67 | 36.8 | 12.2 | 0.9 | 0.0412 | 82 | 5.3 | 50.0 |
| 68 | | | | | | | |
| 69 | 18.9 | 15.2 | 3.1 | 0.0253 | 51 | 3.3 | 62.5 |
| 70 | | | | | | | |
| 71 | 12.0 | 6.1 | 1.8 | 0.0353 | 71 | 4.6 | 79.9 |
| 72 | | | | | | | |
| 73 | 14.0 | 4.7 | 1.5 | 0.0261 | 52 | 3.4 | 79.7 |
| 74 | | | | | | | |
| 75 | 7.8 | 5.2 | 1.2 | 0.0257 | 51 | 3.3 | 85.7 |
| 76 | | | | | | | |
| 77 | 18.9 | 6.4 | 2.3 | 0.0215 | 43 | 2.8 | 72.1 |
| 78 | | | | | | | |
| 79 | 8.3 | 2.0 | 0.4 | 0.0257 | 51 | 3.3 | 89.3 |
| 80 | | | | | | | |
| 81 | 15.1 | 4.5 | 1.6 | 0.0369 | 74 | 4.8 | 78.5 |
| 82 | | | | | | | |
| 83 | 9.2 | 4.2 | 1.7 | 0.0371 | 74 | 4.8 | 84.6 |
| 84 | | | | | | | |

Conditions:
1 mL TD, Catalyst 1, 1.1 equiv Activator-1, 5 mL total volume, solvent = decane, reaction time = 7200 s.
*Corrected values based on wt % unreacted monomer from GC analysis

TABLE 3

Effect of ethylene (C2) on TD oligomerization.

| Expt | TNOAL (umol) | C2 (psi) | mass of isolated sample (g) | Est activity (g pdt/ mmol cat-h) | Est TD conv (%) | wt % unreacted monomer (GC) | wt % dimer (GC) | wt % trimer (GC) | wt % tetramer (GC) | wt % pentamer+ (GC) | Corrected Yield* (g) | Corrected activity* (g pdt/ mmol cat-h) | Corrected TD conv* (%) | Selectivity for dimer (%) |
|---|---|---|---|---|---|---|---|---|---|---|---|---|---|---|
| 1 | 1 | 0 | 0.2375 | 990 | 30.6 | | | | | | | | | |
| 2 | 1 | 0 | 0.2337 | 974 | 30.2 | | | | | | | | | |
| 3 | 1 | 0 | 0.2389 | 995 | 30.8 | | | | | | | | | |
| 4 | 1 | 10 | 0.2618 | 1091 | 33.8 | | | | | | | | | |
| 5 | 1 | 10 | 0.3557 | 1482 | 45.9 | | | | | | | | | |
| 6 | 1 | 10 | 0.2837 | 1182 | 36.6 | 3.5 | 51.7 | 19.4 | 14.0 | 11.3 | 0.2738 | 1140 | 35.3 | 26.3 |
| 7 | 2.5 | 0 | 0.2415 | 1006 | 31.2 | | | | | | | | | |
| 8 | 2.5 | 0 | 0.2170 | 904 | 28.0 | 5.8 | 53.3 | 18.6 | 11.5 | 10.8 | 0.2044 | 852 | 26.4 | 27.4 |
| 9 | 2.5 | 0 | 0.1892 | 788 | 24.4 | | | | | | | | | |
| 10 | 2.5 | 10 | 0.3595 | 1498 | 46.4 | | | | | | | | | |
| 11 | 2.5 | 10 | 0.3576 | 1490 | 46.1 | | | | | | | | | |
| 12 | 2.5 | 10 | 0.3576 | 1490 | 46.1 | | | | | | | | | |
| 13 | 5 | 0 | 0.2079 | 866 | 26.8 | | | | | | | | | |
| 14 | 5 | 0 | 0.2065 | 860 | 26.6 | 6.6 | 57.0 | 21.2 | 11.3 | 3.9 | 0.1929 | 804 | 24.9 | 29.5 |
| 15 | 5 | 0 | 0.2048 | 853 | 26.4 | | | | | | | | | |
| 16 | 5 | 10 | 0.3615 | 1506 | 46.6 | | | | | | | | | |
| 17 | 5 | 10 | 0.3674 | 1531 | 47.4 | | | | | | | | | |
| 18 | 5 | 10 | 0.3739 | 1558 | 48.2 | | | | | | | | | |
| 19 | 10 | 0 | 0.1418 | 591 | 18.3 | | | | | | | | | |
| 20 | 10 | 0 | 0.1530 | 638 | 19.7 | | | | | | | | | |
| 21 | 10 | 0 | 0.1485 | 619 | 19.2 | | | | | | | | | |
| 22 | 10 | 10 | 0.3545 | 1477 | 45.7 | | | | | | | | | |
| 23 | 10 | 10 | 0.3542 | 1476 | 45.7 | | | | | | | | | |
| 24 | 10 | 10 | 0.3468 | 1445 | 44.7 | 4.0 | 59.4 | 19.0 | 10.0 | 7.6 | 0.3329 | 1387 | 43.0 | 30.3 |

Conditions: 1 mL TD, 0.12 μmol Catalyst-1, 1.1 equiv Activator-1, 5 mL total volume, solvent = isohexane, T = 80° C., reaction time = 7200 s.
*Corrected values based on wt % unreacted monomer from GC analysis

TABLE 4

Oligomerization of 1-octene and 1-decene.

| Expt | Catalyst (0.040 umol) | monomer (1 mL) | C2 (psi) | actual quench time (s) | mass of isolated sample (g) | Est activity (g pdt/mmol cat-h) | Est monomer conv (%) |
|---|---|---|---|---|---|---|---|
| 1 | Catalyst-1 | decene | 0 | 3600 | 0.0624 | 1560 | 8.4 |
| 2 | Catalyst-1 | decene | 0 | 3602 | 0.0501 | 1252 | 6.8 |

TABLE 4-continued

Oligomerization of 1-octene and 1-decene.

| Expt | Catalyst (0.040 umol) | monomer (1 mL) | C2 (psi) | actual quench time (s) | mass of isolated sample (g) | Est activity (g pdt/mmol cat-h) | Est monomer conv (%) |
|---|---|---|---|---|---|---|---|
| 3  | Catalyst-1 | decene | 0  | 3600 | 0.0590 | 1475 | 8.0 |
| 4  | Catalyst-1 | decene | 10 | 3600 | 0.1794 | 4485 | 24.2 |
| 5  | Catalyst-1 | decene | 10 | 3600 | 0.1870 | 4675 | 25.2 |
| 6  | Catalyst-1 | decene | 10 | 3602 | 0.1698 | 4243 | 22.9 |
| 7  | Catalyst-2 | decene | 0  | 3601 | 0.0184 | 460  | 2.5 |
| 8  | Catalyst-2 | decene | 0  | 3600 | 0.0144 | 360  | 1.9 |
| 9  | Catalyst-2 | decene | 0  | 3601 | 0.0172 | 430  | 2.3 |
| 10 | Catalyst-2 | decene | 10 | 3601 | 0.0402 | 1005 | 5.4 |
| 11 | Catalyst-2 | decene | 10 | 3600 | 0.0517 | 1293 | 7.0 |
| 12 | Catalyst-2 | decene | 10 | 3601 | 0.0383 | 957  | 5.2 |
| 13 | Catalyst-1 | octene | 0  | 3600 | 0.0690 | 1725 | 9.7 |
| 14 | Catalyst-1 | octene | 0  | 3600 | 0.0654 | 1635 | 9.1 |
| 15 | Catalyst-1 | octene | 0  | 3601 | 0.0665 | 1662 | 9.3 |
| 16 | Catalyst-1 | octene | 10 | 3601 | 0.2053 | 5131 | 28.7 |
| 17 | Catalyst-1 | octene | 10 | 3601 | 0.2190 | 5473 | 30.6 |
| 18 | Catalyst-1 | octene | 10 | 3600 | 0.1699 | 4248 | 23.8 |
| 19 | Catalyst-2 | octene | 0  | 3601 | 0.0170 | 425  | 2.4 |
| 20 | Catalyst-2 | octene | 0  | 3600 | 0.0167 | 418  | 2.3 |
| 21 | Catalyst-2 | octene | 0  | 3600 | 0.0159 | 398  | 2.2 |
| 22 | Catalyst-2 | octene | 10 | 3601 | 0.0409 | 1022 | 5.7 |
| 23 | Catalyst-2 | octene | 10 | 3600 | 0.0612 | 1530 | 8.6 |
| 24 | Catalyst-2 | octene | 10 | 3601 | 0.0435 | 1087 | 6.1 |

Conditions:
1 mL monomer, 0.04 μmol Catalyst 1 or Catalyst 2, 1.1 equiv Activator-1, 1.0 μmol TNOAL, 5 mL total volume, solvent = isohexane, T = 80° C., reaction time = 3600 s.

TABLE 5

Unsaturation data from $^1$H NMR for selected experiments from Table 2.

| Expt | Catalyst-1 (umol) | TNOAL (umol) | vinylenes/ 1000 C. | trisubs/ 1000 C. | vinyls/ 1000 C. | vinylidenes/ 1000 C. | total unsat/ 1000 C. | % vinylene | % trisub | % vinyl | % vinylidene |
|---|---|---|---|---|---|---|---|---|---|---|---|
| 2  | 0.25 | 0.0  | 1.49 | 0.31 | 0.14 | 24.19 | 26.13 | 5.7 | 1.2 | 0.5 | 92.6 |
| 4  | 0.4  | 0.0  | 1.57 | 0.54 | 0.10 | 24.27 | 26.48 | 5.9 | 2.0 | 0.4 | 91.7 |
| 6  | 0.5  | 0.0  | 1.67 | 0.44 | 0.10 | 25.07 | 27.28 | 6.1 | 1.6 | 0.4 | 91.9 |
| 8  | 0.6  | 0.0  | 1.68 | 0.40 | 0.14 | 25.43 | 27.65 | 6.1 | 1.4 | 0.5 | 92.0 |
| 10 | 0.8  | 0.0  | 1.74 | 0.54 | 0.13 | 25.25 | 27.66 | 6.3 | 2.0 | 0.5 | 91.3 |
| 12 | 1    | 0.0  | 1.62 | 0.48 | 0.12 | 25.19 | 27.41 | 5.9 | 1.8 | 0.4 | 91.9 |
| 14 | 1.2  | 0.0  | 1.74 | 0.60 | 0.15 | 25.48 | 27.97 | 6.2 | 2.1 | 0.5 | 91.1 |
| 44 | 0.25 | 5.0  | 1.62 | 1.25 | 0.10 | 21.59 | 24.56 | 6.6 | 5.1 | 0.4 | 87.9 |
| 48 | 0.25 | 10.0 | 1.48 | 0.13 | 0.15 | 22.10 | 23.86 | 6.2 | 0.5 | 0.6 | 92.6 |

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention.

Accordingly, it is not intended that the invention be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A homogeneous process for producing alpha-olefin dimers, the process comprising: contacting, in a homogeneous phase and at a temperature of 80° C. or more, a feedstock consisting essentially of one or more $C_{8+}$ alpha-olefins and optionally ethylene, where the ethylene comprises from 0.1 to 10 wt % of the total feed, with a catalyst system comprising activator and one or more catalyst compounds represented by the formula:

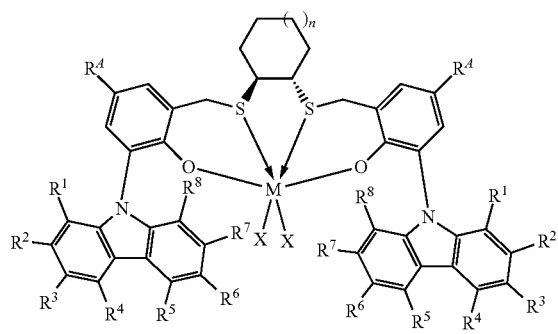

where M is a Group 4 metal; n is 1, 2, or 3; $R^A$ is hydrogen or a $C_1$ to $C_{10}$ alkyl; each of $R^1$, $R^2$, $R^3$, $R^4$, $R^5$, $R^6$, $R^7$, and $R^8$ is independently selected from hydrogen and $C_1$ to $C_{10}$ alkyl, optionally wherein any two or more adjacent groups from $R^1$ through $R^8$ may be joined to form a cyclic or polycyclic ring structure; each X is independently selected from the group consisting of hydrocarbyl radicals having from 1 to 20 carbon atoms, hydrides, amides, alkoxides, sulfides, phosphides, halides, and a combination thereof, optionally two X's may form a part of a fused ring or a ring system, the contacting being conducted under conditions effective to oligomerize at least part of $C_{8+}$ alpha-olefin to produce an oligomer product containing at least 30 wt % of the alpha-olefin dimer, based upon the weight of the oligomer product produced, and at least 80 mol % of vinylidene unsaturation, where the conversion of the alpha olefin is at least 10 wt %, based upon the weight of the alpha olefin monomer entering the reactor and the weight of product produced.

2. The process of claim 1, wherein the feedstock comprises at least one $C_8$ to $C_{20}$ alpha-olefin.

3. The process of claim 1, wherein the feedstock comprises at least one $C_{8+}$ linear alpha-olefin.

4. The process of claim 1, wherein the feedstock comprises ethylene.

5. The process of claim 1, wherein M is Zr.

6. The process of claim 1, wherein n is 1.

7. The process of claim 1, wherein n is 2 or 3.

8. The process of claim 1, wherein each X is independently selected from $C_1$ to $C_5$ alkyl groups, benzyl, and substituted benzyl.

9. The process of claim 1, wherein $R^4$ is Me or tBu.

10. The process of claim 1, wherein each of $R^1$, $R^2$, $R^4$, $R^5$, $R^7$, and $R^8$ is H and $R^3$ and $R^6$ are tBu.

11. A process for producing alpha-olefin dimers, the process comprising: contacting, at a temperature of 80° C. or more, feedstock comprising one or more $C_{8+}$ alpha-olefins with a catalyst system comprising activator and one or more catalyst compounds selected from:

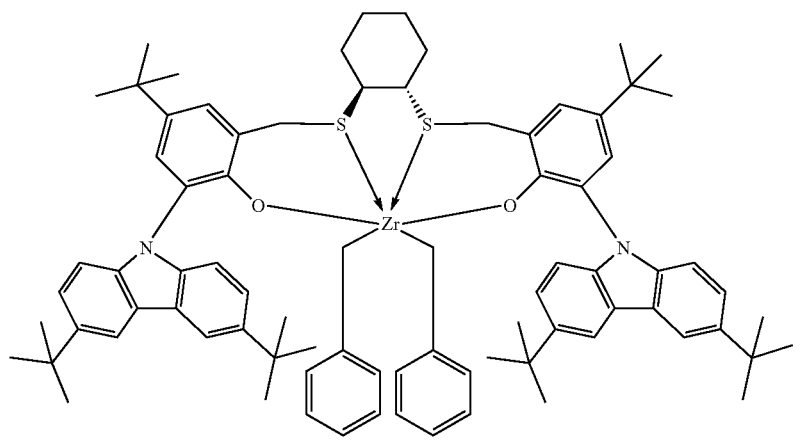

Catalyst 1

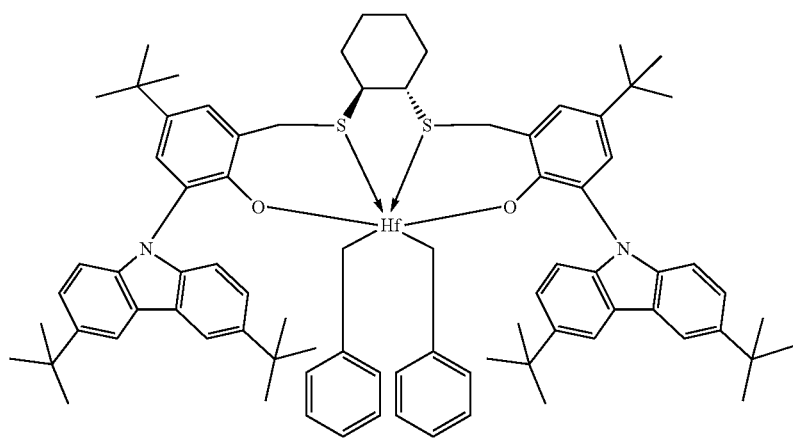

Catalyst 2

Catalyst 3

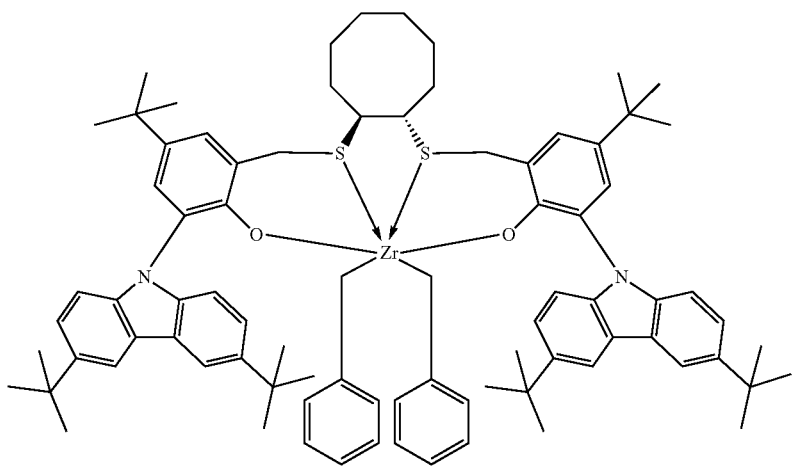

Catalyst 4

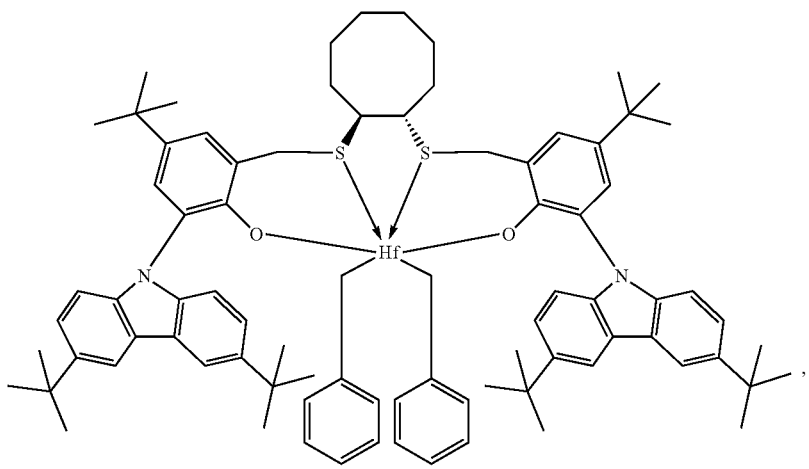

the contacting being conducted under conditions effective to oligomerize at least part of $C_{8+}$ alpha-olefin to produce an oligomer product containing at least 30 wt % of the alpha-olefin dimer, based upon the weight of the oligomer product produced, and at least 80 mol % of vinylidene unsaturation, where the conversion of the alpha olefin is at least 10 wt %, based upon the weight of the alpha olefin monomer entering the reactor and the weight of product produced.

12. The process of claim 1, wherein the activator is represented by the formula:

$$(Z)^{d+}(A^{d-})$$

wherein Z is (L-H) or a reducible Lewis Acid, L is a neutral Lewis base; H is hydrogen; (L-H)+ is a Brønsted acid; $A^{d-}$ is a non-coordinating anion having the charge d−; and d is an integer from 1 to 3; optionally Z is represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl.

13. The process of claim 1, wherein the activator is one or more of: N,N-dimethylanilinium tetrakis(pentafluorophenyl)borate; triphenylcarbenium tetrakis(pentafluorophenyl)borate; trimethylammonium tetrakis(perfluoronaphthyl)borate; triethylammonium tetrakis(perfluoronaphthyl)borate; tripropylammonium tetrakis(perfluoronaphthyl)borate; tri (n-butyl)ammonium tetrakis(perfluoronaphthyl)borate; tri(t-butyl)ammonium tetrakis(perfluoronaphthyl)borate; N,N-dimethylanilinium tetrakis(perfluoronaphthyl)borate; N,N-diethylanilinium tetrakis(perfluoronaphthyl)borate; N,N-dimethyl-(2,4,6-trimethylanilinium) tetrakis (perfluoronaphthyl)borate; tropillium tetrakis (perfluoronaphthyl)borate; triphenylcarbenium tetrakis (perfluoronaphthyl)borate; triphenylphosphonium tetrakis (perfluoronaphthyl)borate; triethylsilylium tetrakis (perfluoronaphthyl)borate; benzene(diazonium) tetrakis (perfluoronaphthyl)borate; trimethylammonium tetrakis (perfluorobiphenyl)borate; triethylammonium tetrakis (perfluorobiphenyl)borate; tripropylammonium tetrakis(perfluorobiphenyl)borate; tri (n-butyl)ammonium tetrakis(perfluorobiphenyl)borate; tri(t-butyl)ammonium tetrakis(perfluorobiphenyl)borate; N,N-dimethylanilinium tetrakis(perfluorobiphenyl)borate; N,N-diethylanilinium tetrakis(perfluorobiphenyl)borate; N,N-dimethyl-(2,4,6-trimethylanilinium) tetrakis(perfluorobiphenyl)borate; tropillium tetrakis(perfluorobiphenyl)borate; triphenylcarbenium tetrakis(perfluorobiphenyl)borate; triphenylphosphonium tetrakis(perfluorobiphenyl)borate; triethylsilylium tetrakis(perfluorobiphenyl)borate; benzene(diazonium) tetrakis(perfluorobiphenyl)borate; [4-t-butyl-PhNMe$_2$H][(C$_6$F$_3$(C$_6$F$_5$)$_2$)$_4$B]; trimethylammonium tetraphenylborate; triethylammonium tetraphenylborate; tripropylammonium tetraphenylborate;

tri(n-butyl)ammonium tetraphenylborate; tri(t-butyl) ammonium tetraphenylborate; N,N-dimethylanilinium tetraphenylborate; N,N-diethylanilinium tetraphenylborate; N,N-dimethyl-(2,4,6-trimethylanilinium) tetraphenylborate; tropillium tetraphenylborate; triphenylcarbenium tetraphenylborate; triphenylphosphonium tetraphenylborate; triethylsilylium tetraphenylborate; benzene(diazonium)tetraphenylborate; trimethylammonium tetrakis(pentafluorophenyl)borate; triethylammonium tetrakis(pentafluorophenyl)borate; tripropylammonium tetrakis(pentafluorophenyl)borate; tri(n-butyl)ammonium tetrakis(pentafluorophenyl)borate; tri (sec-butyl)ammonium tetrakis(pentafluorophenyl) borate; N,N-dimethylanilinium tetrakis (pentafluorophenyl)borate; bis(hydrogenatedtallow) methylammonium tetrakis(pentafluorophenyl)borate; Bis(hydrogenatedtallow)methylammonium tetrakis (perfluoronaphth-2-yl)borate; N,N-diethylanilinium tetrakis(pentafluorophenyl)borate; N,N-dimethyl-(2,4,6-trimethylanilinium) tetrakis(pentafluorophenyl)borate; tropillium tetrakis(pentafluorophenyl)borate; triphenylcarbenium tetrakis(pentafluorophenyl)borate; triphenylphosphonium tetrakis(pentafluorophenyl)borate; triethylsilylium tetrakis(pentafluorophenyl)borate; benzene(diazonium) tetrakis(pentafluorophenyl)borate; trimethylammonium tetrakis-(2,3,4,6-tetrafluorophenyl) borate; triethylammonium tetrakis-(2,3,4,6-tetrafluorophenyl)borate; tripropylammonium tetrakis-(2,3,4,6-tetrafluorophenyl)borate; tri(n-butyl)ammonium tetrakis-(2,3,4,6-tetrafluoro-phenyl)borate; dimethyl(t-butyl)ammonium tetrakis-(2,3,4,6-tetrafluorophenyl) borate; N,N-dimethylanilinium tetrakis-(2,3,4,6-tetrafluorophenyl)borate; N,N-diethylanilinium tetrakis-(2,3,4,6-tetrafluorophenyl)borate; N,N-dimethyl-(2,4,6-trimethylanilinium) tetrakis-(2,3,4,6-tetrafluorophenyl) borate; tropillium tetrakis-(2,3,4,6-tetrafluorophenyl) borate; triphenylcarbenium tetrakis-(2,3,4,6-tetrafluorophenyl)borate; triphenylphosphonium tetrakis-(2,3,4,6-tetrafluorophenyl)borate; triethylsilylium tetrakis-(2,3,4,6-tetrafluorophenyl)borate; benzene (diazonium) tetrakis-(2,3,4,6-tetrafluorophenyl) borate; trimethylammonium tetrakis(3,5-bis (trifluoromethyl)phenyl)borate; triethylammonium tetrakis(3,5-bis(trifluoromethyl)phenyl)borate; tripropylammonium tetrakis(3,5-bis(trifluoromethyl)phenyl) borate; tri(n-butyl)ammonium tetrakis(3,5-bis(trifluoromethyl)phenyl)borate; tri(t-butyl)ammonium tetrakis (3,5-bis(trifluoromethyl)phenyl)borate; N,N-dimethylanilinium tetrakis(3,5-bis(trifluoromethyl) phenyl)borate; N,N-diethylanilinium tetrakis(3,5-bis (trifluoromethyl)phenyl)borate; N,N-dimethyl-(2,4,6-trimethylanilinium) tetrakis(3,5-bis(trifluoromethyl) phenyl)borate; tropillium tetrakis(3,5-bis (trifluoromethyl)phenyl)borate; triphenylcarbenium tetrakis(3,5-bis(trifluoromethyl)phenyl)borate; triphenylphosphonium tetrakis(3,5-bis(trifluoromethyl)phenyl)borate; triethylsilylium tetrakis(3,5-bis(trifluoromethyl)phenyl)borate; benzene(diazonium) tetrakis(3,5-bis(trifluoromethyl)phenyl)borate; di-(i-propyl) ammonium tetrakis(pentafluorophenyl)borate; dicyclohexylammonium tetrakis(pentafluorophenyl) borate; tri(o-tolyl)phosphonium tetrakis(pentafluorophenyl)borate; tri(2,6-dimethylphenyl)phosphonium tetrakis(pentafluorophenyl)borate; triphenylcarbenium tetrakis(perfluorophenyl)borate; 1-(4-(tris(pentafluorophenyl)borate)-2,3,5,6-tetrafluorophenyl)pyrrolidinium; tetrakis(pentafluorophenyl)borate; 4-(tris(pentafluorophenyl)borate)-2,3,5,6-tetrafluoropyridine; and triphenylcarbenium tetrakis(3,5-bis(trifluoromethyl) phenyl)borate).

14. The process of claim 1, wherein the contacting is conducted at a temperature of at least 80° C. and a pressure from 0.5 to 10 MPa-a.

15. The process of claim 1, wherein the oligomer product contains at least 40 wt % of alpha-olefin dimer, based upon the weight of the oligomer product.

16. The process of claim 1, wherein the monomer conversion is at least 20 wt %.

17. The process of claim 1, wherein the oligomerized product has at least 90 mol % vinylidene unsaturation.

18. The process of claim 1, wherein the oligomerized product comprises one or more dimers represented by the formula:

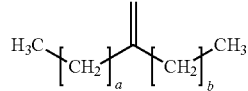

where "a" is an integer from 7 to 19 and "b" is an integer from 5 to 17.

19. The process of claim 18, wherein "a" is 13 and "b" is 11.

20. The process of claim 18, wherein "a" is 9 and "b" is 7.

21. The process of claim 18, wherein "a" is 7 and "b" is 7.

22. The process of claim 1, wherein no scavenger is present.

23. The process of claim 1, wherein the process temperature is from 85° C. to 160° C.

24. The process of claim 1, wherein the process temperature is from 90° C. to 150° C.

25. The process of claim 1, wherein the process temperature is from 110° C. to 150° C.

26. The process of claim 1, wherein:
the feedstock comprises at least one $C_8$ to $C_{20}$ alpha-olefin; and
at least one $C_{8+}$ linear alpha-olefin.

27. The process of claim 26, wherein the feedstock further comprises 0.1 to 5 wt % ethylene.

28. The process of claim 26, wherein:
M is Zr;
each X is independently selected from $C_1$ to $C_5$ alkyl groups, benzyl, and substituted benzyl;
$R^A$ is H, Me or tBu, and the activator is represented by the formula:

$$(Z)^{d+}(A^{d-})$$

wherein Z is (L-H) or a reducible Lewis Acid, L is a neutral Lewis base; H is hydrogen; (L-H)+ is a Bronsted acid; $A^{d-}$ is a non-coordinating anion having the charge d−; and d is an integer from 1 to 3; optionally Z is represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl.

29. The process of claim 13, wherein:
i) the feedstock comprises at least one $C_8$ to $C_{20}$ alpha-olefin and at least one $C_{8+}$ linear alpha-olefin;
ii) M is Zr;
iii) each X is independently selected from $C_1$ to $C_5$ alkyl groups, benzyl, and substituted benzyl;
iv) the process temperature is from 85° C. to 160° C.; and (v) the oligomerized product comprises one or more dimers represented by the formula:

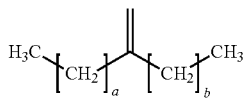

where "a" is an integer from 7 to 19 and "b" is an integer from 5 to 17.

30. The process of claim 1, wherein:
    i) the feedstock comprises at least one $C_8$ to $C_{20}$ alpha-olefin and at least one $C_{8+}$ linear alpha-olefin;
    ii) M is Zr;
    iii) each X is independently selected from $C_1$ to $C_5$ alkyl groups, benzyl, and substituted benzyl;
    iv) the feedstock further comprises ethylene; and
    v) the activator is represented by the formula:

$(Z)^{d+}(A^{d-})$ wherein Z is (L-H) or a reducible Lewis Acid, L is a neutral Lewis base; H is hydrogen; (L-H)+ is a Bronsted acid; $A^{d-}$ is a non-coordinating anion having the charge d−; and d is an integer from 1 to 3; optionally Z is represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl;
    the process temperature is from 90° C. to 150° C.; and
    the oligomerized product comprises one or more dimers represented by the formula:

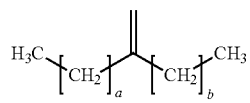

where "a" is an integer from 7 to 19 and "b" is an integer from 5 to 17.

31. The process of claim 30, wherein:
    a) the oligomer product contains at least 40 wt % of alpha-olefin dimer, based upon the weight of the oligomer product;
    b) the monomer conversion is at least 20 wt %; and
    c) the oligomerized product has at least 90 mol % vinylidene unsaturation.

32. A process for producing alpha-olefin dimers, the process comprising: contacting, at a temperature of 80° C. or more, feedstock comprising one or more $C_{8+}$ alpha-olefins with a catalyst system comprising activator and one or more catalyst compounds selected from:

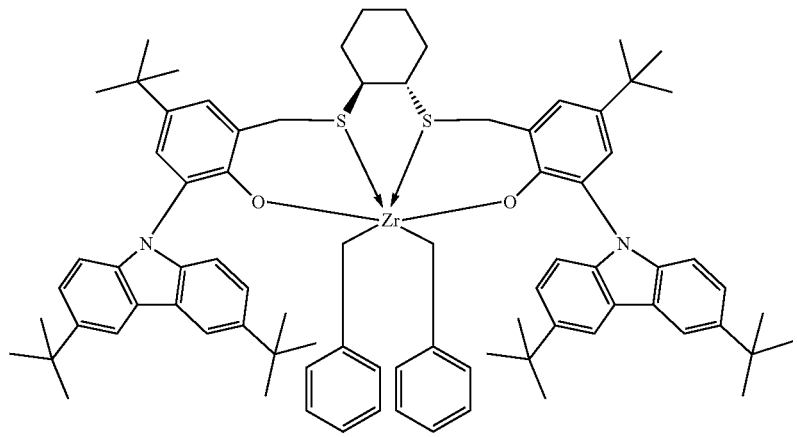

Catalyst 1

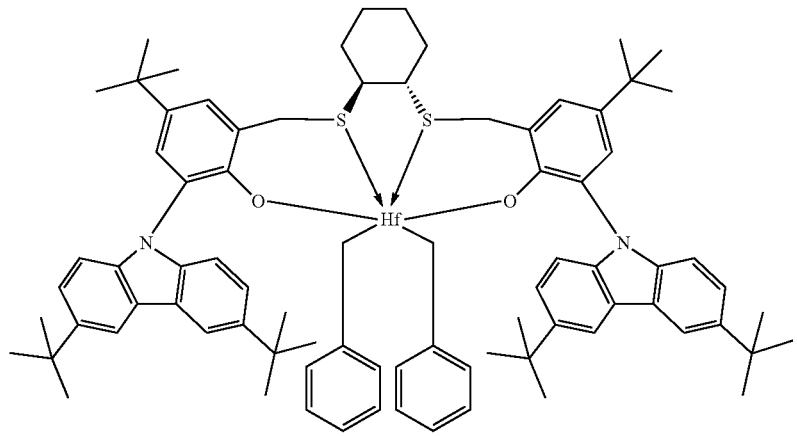

Catalyst 2

-continued

Catalyst 3

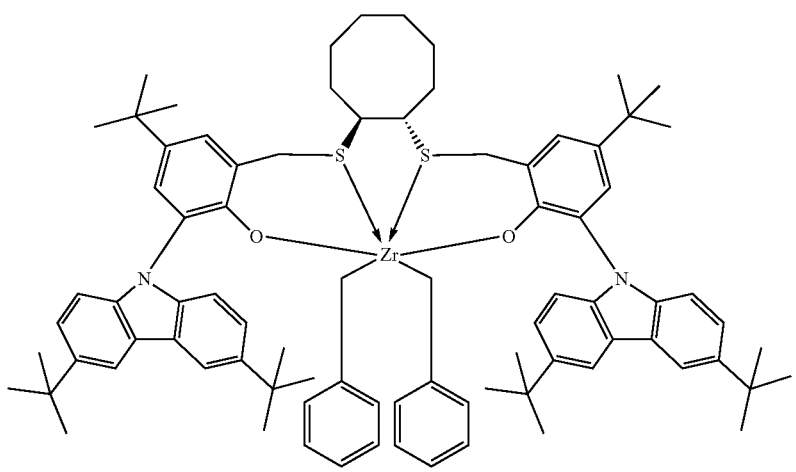

Catalyst 4

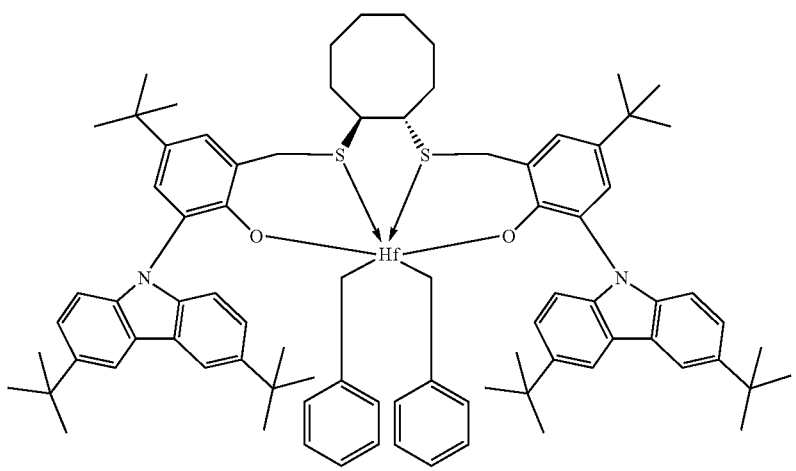

the contacting being conducted under conditions effective to oligomerize at least part of $C_{8+}$ alpha-olefin to produce an oligomer product containing at least 40 wt % of alpha-olefin dimer, based upon the weight of the oligomer product;

and at least 80 mol % of vinylidene unsaturation, where the monomer conversion of the alpha olefin is at least 20 wt %, based upon the weight of the alpha olefin monomer entering the reactor and the weight of product produced;

the process temperature is from 85° C. to 160° C.; and wherein the activator is one or more of:

N,N-dimethylanilinium tetrakis(pentafluorophenyl)borate; triphenylcarbenium tetrakis(pentafluorophenyl)borate; trimethylammonium tetrakis(perfluoronaphthyl)borate; triethylammonium tetrakis(perfluoronaphthyl)borate; tripropylammonium tetrakis(perfluoronaphthyl)borate; tri(n-butyl)ammonium tetrakis(perfluoronaphthyl)borate; tri(t-butyl)ammonium tetrakis(perfluoronaphthyl)borate; N,N-dimethylanilinium tetrakis(perfluoronaphthyl)borate; N,N-diethylanilinium tetrakis(perfluoronaphthyl)borate; N,N-dimethyl-(2,4,6-trimethylanilinium) tetrakis(perfluoronaphthyl)borate; tropillium tetrakis(perfluoronaphthyl)borate; triphenylcarbenium tetrakis(perfluoronaphthyl)borate; triphenylphosphonium tetrakis (perfluoronaphthyl)borate; triethylsilylium tetrakis (perfluoronaphthyl)borate; benzene(diazonium) tetrakis(perfluoronaphthyl)borate; trimethylammonium tetrakis(perfluorobiphenyl)borate; triethylammonium tetrakis(perfluorobiphenyl)borate; tripropylammonium tetrakis(perfluorobiphenyl)borate; tri(n-butyl)ammonium tetrakis(perfluorobiphenyl)borate; tri(t-butyl)ammonium tetrakis(perfluorobiphenyl)borate; N,N-dimethylanilinium tetrakis(perfluorobiphenyl)borate; N,N-diethylanilinium tetrakis(perfluorobiphenyl)borate; N,N-dimethyl-(2,4,6-trimethylanilinium) tetrakis(perfluorobiphenyl)borate; tropillium tetrakis(perfluorobiphenyl)borate; triphenylcarbenium tetrakis(perfluorobiphenyl)borate; triphenylphosphonium tetrakis (perfluorobiphenyl)borate; triethylsilylium tetrakis (perfluorobiphenyl)borate; benzene(diazonium) tetrakis(perfluorobiphenyl)borate; [4-t-butyl-PhNMe$_2$H][(C$_6$F$_3$ (C$_6$F$_5$)$_2$)$_4$B]; trimethylammonium tetraphenylborate; triethylammonium tetraphenylborate; tripropylammonium tetraphenylborate; tri(n-butyl)ammonium tetraphenylborate; tri(t-butyl)ammonium tetraphenylborate; N,N-dimethylanilinium tetraphenylborate; N,N-diethylanilinium tetraphenylborate; N,N-dimethyl-(2,4,6-trimethylanilinium) tetraphenylborate; tropillium tetraphenylborate; triphenylcarbenium tetraphenylborate; triphenylphosphonium tetraphenylborate; triethylsilylium tetraphenylborate; benzene(diazonium)tetraphenylborate; trimethylammonium tetrakis(pentafluorophenyl)borate; triethylammonium tetrakis(pentafluorophenyl)borate; tripropylammonium tetrakis(pentafluorophenyl)borate; tri(n-butyl)ammonium tetrakis(pentafluorophenyl)borate; tri (sec-butyl)ammonium tetrakis(pentafluorophenyl) borate; N,N-dimethylanilinium tetrakis (pentafluorophenyl)borate; bis(hydrogenatedtallow) methylammonium tetrakis(pentafluorophenyl)borate; Bis(hydrogenatedtallow)methylammonium tetrakis (perfluoronaphth-2-yl)borate; N,N-diethylanilinium tetrakis(pentafluorophenyl)borate; N,N-dimethyl-(2,4,6-trimethylanilinium) tetrakis(pentafluorophenyl)borate; tropillium tetrakis(pentafluorophenyl)borate; triphenylcarbenium tetrakis(pentafluorophenyl)borate; triphenylphosphonium tetrakis(pentafluorophenyl)borate; triethylsilylium tetrakis(pentafluorophenyl)borate; benzene(diazonium) tetrakis(pentafluorophenyl)borate; trimethylammonium tetrakis-(2,3,4,6-tetrafluorophenyl) borate; triethylammonium tetrakis-(2,3,4,6-tetrafluorophenyl)borate; tripropylammonium tetrakis-(2,3,4,6-tetrafluorophenyl)borate; tri(n-butyl)ammonium tetrakis-(2,3,4,6-tetrafluoro-phenyl)borate; dimethyl(t-butyl)ammonium tetrakis-(2,3,4,6-tetrafluorophenyl) borate; N,N-dimethylanilinium tetrakis-(2,3,4,6-tetrafluorophenyl)borate; N,N-diethylanilinium tetrakis-(2,3,4,6-tetrafluorophenyl)borate; N,N-dimethyl-(2,4,6-trimethylanilinium) tetrakis-(2,3,4,6-tetrafluorophenyl) borate; tropillium tetrakis-(2,3,4,6-tetrafluorophenyl) borate; triphenylcarbenium tetrakis-(2,3,4,6-tetrafluorophenyl)borate; triphenylphosphonium tetrakis-(2,3,4,6-tetrafluorophenyl)borate; triethylsilylium tetrakis-(2,3,4,6-tetrafluorophenyl)borate; benzene(diazonium) tetrakis-(2,3,4,6-tetrafluorophenyl) borate; trimethylammonium tetrakis(3,5-bis (trifluoromethyl)phenyl)borate; triethylammonium tetrakis(3,5-bis(trifluoromethyl)phenyl)borate; tripopylammonium tetrakis(3,5-bis(trifluoromethyl)phenyl) borate; tri(n-butyl)ammonium tetrakis(3,5-bis(trifluoromethyl)phenyl)borate; tri(t-butyl)ammonium tetrakis (3,5-bis(trifluoromethyl)phenyl)borate; N,N-dimethylanilinium tetrakis(3,5-bis(trifluoromethyl) phenyl)borate, N,N-diethylanilinium tetrakis(3,5-bis (trifluoromethyl)phenyl)borate, N,N-dimethyl-(2,4,6-trimethylanilinium) tetrakis(3,5-bis(trifluoromethyl) phenyl)borate, tropillium tetrakis(3,5-bis (trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium) tetrakis(3,5-bis(trifluoromethyl)phenyl)borate, di-(i-propyl) ammonium tetrakis(pentafluorophenyl)borate, dicyclohexylammonium tetrakis(pentafluorophenyl) borate, tri(o-tolyl)phosphonium tetrakis(pentafluorophenyl)borate, tri(2,6-dimethylphenyl)phosphonium tetrakis(pentafluorophenyl)borate, triphenylcarbenium tetrakis(perfluorophenyl)borate, 1-(4-(tris(pentafluorophenyl)borate)-2,3,5,6-tetrafluorophenyl)pyrrolidinium, tetrakis(pentafluorophenyl)borate, 4-(tris(pentafluorophenyl)borate)-2,3,5,6-tetrafluoropyridine, and triphenylcarbenium tetrakis(3,5-bis(trifluoromethyl) phenyl)borate).

33. A homogeneous solution process for producing alpha-olefin dimers, the process comprising: contacting, in a homogeneous phase and at a temperature of 80° C. or more, a feedstock consisting essentially of one or more $C_{8+}$ alpha-olefins and optionally from 0.1 to 10 wt % of ethylene, based upon the total feed, with a catalyst system comprising activator and one or more catalyst compounds represented by the formula:

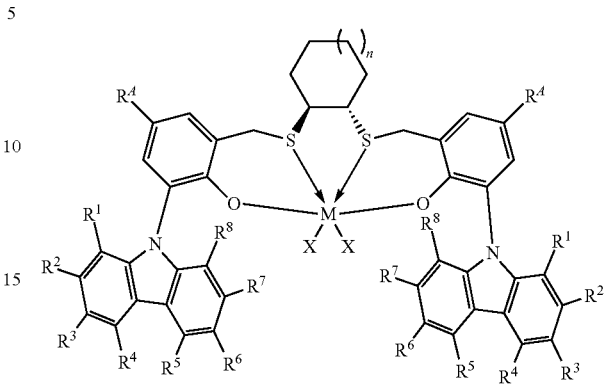

where M is Zr; n is 1, 2, or 3; $R^4$ is tBu; each of $R^1$, $R^2$, $R^4$, $R^5$, $R^7$, and $R^8$ is independently selected from hydrogen and $C_1$ to $C_{10}$ alkyl, optionally wherein any two or more adjacent groups from $R^1$ through $R^8$ may be joined to form a cyclic or polycyclic ring structure; each of $R^3$ and $R^6$ is tBu; each X is independently selected from the group consisting of hydrocarbyl radicals having from 1 to 20 carbon atoms, hydrides, amides, alkoxides, sulfides, phosphides, halides, and a combination thereof, optionally two X's may form a part of a fused ring or a ring system, the contacting being conducted under conditions effective to oligomerize at least part of $C_{8+}$ alpha-olefin to produce an oligomer product containing at least 30 wt % of the alpha-olefin dimer, based upon the weight of the oligomer product produced, and at least 80 mol % of vinylidene unsaturation, where the conversion of the alpha olefin is at least 10 wt %, based upon the weight of the alpha olefin monomer entering the reactor and the weight of product produced.

34. The process of claim 33 where n is 1.
35. The process of claim 33 where n is 2.
36. The process of claim 33 where n is 3.
37. The process of claim 1, wherein the one or more $C_{8+}$ alpha-olefins comprise in excess of 50 wt % of 1-tetradecene.
38. The process of claim 1, wherein the one or more $C_{8+}$ alpha-olefins comprise two or more $C_{8+}$ alpha-olefins.
39. The process of claim 1, wherein the one or more $C_{8+}$ alpha-olefins are linear alpha-olefins.
40. The process of claim 1, wherein the one or more $C_{8+}$ alpha-olefins are $C_8$, $C_{10}$, $C_{12}$ and or $C_{14}$ linear alpha olefins.
41. The process of claim 33, wherein the process contains ethylene in addition to the one or more $C_{8+}$ alpha-olefins, where the amount of ethylene present in the feed is from 0.1 to 10 wt % of the total feed.
42. The process of claim 1 wherein the ethylene is present in the feed at 0.1 to 5 wt %.
43. The process of claim 1, wherein the ethylene is present in the feed at 0.5 to 3 wt %.
44. A homogeneous process for producing alpha-olefin dimers, the process comprising: contacting, in a homogeneous phase and at a temperature of 90° C. or more, a feedstock consisting essentially of one or more $C_{8+}$ alpha-olefins and optionally from 0.1 to 10 wt % of ethylene, based upon the total feed, with a catalyst system comprising non-coordinating anion activator and one or more catalyst compounds represented by the formula:

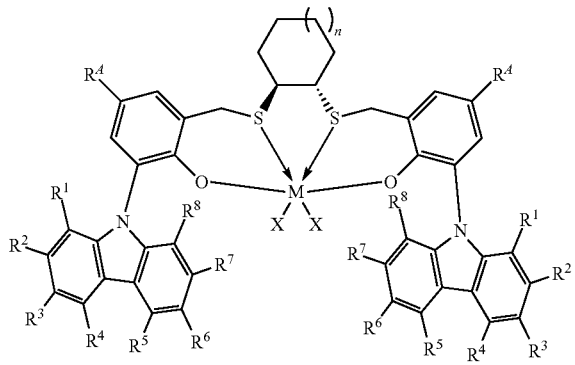

where M is a Group 4 metal; n is 1, 2, or 3; $R^A$ is H or $C_1$ to $C_{10}$ alkyl; each of $R^1$, $R^2$, $R^4$, $R^5$, $R^7$, and $R^8$ is independently selected from hydrogen and $C_1$ to $C_{10}$ alkyl, optionally wherein any two or more adjacent groups from $R^1$ through $R^8$ may be joined to form a cyclic or polycyclic ring structure; each of $R^3$ and $R^6$ is independently H or a $C_1$ to $C_{10}$ alkyl; each X is independently selected from the group consisting of hydrocarbyl radicals having from 1 to 20 carbon atoms, hydrides, amides, alkoxides, sulfides, phosphides, halides, and a combination thereof, optionally two X's may form a part of a fused ring or a ring system, the contacting being conducted under conditions effective to oligomerize at least part of $C_{8+}$ alpha-olefin to produce an oligomer product containing at least 30 wt % of the alpha-olefin dimer, based upon the weight of the oligomer product produced, and at least 80 mol % of vinylidene unsaturation, where the conversion of the alpha olefin is at least 10 wt %, based upon the weight of the alpha olefin monomer entering the reactor and the weight of product produced, wherein alkyl alumoxane is not present.

* * * * *